(12) United States Patent
Su et al.

(10) Patent No.: US 11,886,504 B2
(45) Date of Patent: Jan. 30, 2024

(54) SYSTEMS AND METHODS FOR GENERATING SMELL DATA AND A DATABASE THEREOF

(71) Applicant: MS/\2 Inc., Santa Clara, CA (US)

(72) Inventors: Xing Su, Santa Clara, CA (US); Kai Wu, Santa Clara, CA (US)

(73) Assignee: MS2 INC., Santa Clara, CA (US)

( * ) Notice: Subject to any disclaimer, the term of this patent is extended or adjusted under 35 U.S.C. 154(b) by 0 days.

(21) Appl. No.: 17/856,271

(22) Filed: Jul. 1, 2022

(65) Prior Publication Data

US 2022/0405326 A1 Dec. 22, 2022

Related U.S. Application Data

(63) Continuation of application No. 17/007,292, filed on Aug. 31, 2020, now Pat. No. 11,409,797.

(51) Int. Cl.
*G06F 16/901* (2019.01)
*G06F 16/906* (2019.01)
(Continued)

(52) U.S. Cl.
CPC ....... *G06F 16/901* (2019.01); *G01N 33/0001* (2013.01); *G06F 16/906* (2019.01); *G06F 16/9035* (2019.01); *G06N 7/00* (2013.01)

(58) Field of Classification Search
CPC .. G06F 16/901; G06F 16/906; G06F 16/9035; G06N 7/00; G01N 33/0001
(Continued)

(56) References Cited

U.S. PATENT DOCUMENTS 10,152,116 B2 * 12/2018 Wang ..................... G06F 3/16
10,775,356 B2 * 9/2020 Gafsou ............. G01N 33/0001
(Continued)

FOREIGN PATENT DOCUMENTS

WO    WO 02/35495 A1 *   5/2002   ............. G08C 17/00

OTHER PUBLICATIONS

Deshmukh, Sharvari, et al., "Application of electronic nose for industrial odors and gaseous emissions measurement and monitoring—An overview", Talanta, vol. 144, Nov. 1, 2015, pp. 329-340.*
(Continued)

*Primary Examiner* — Robert Stevens
(74) *Attorney, Agent, or Firm* — Dave Law Group LLC; Raj S. Dave

(57) ABSTRACT

A database comprising a digital signature of a smell, the digital signature comprising a smell data, the smell data comprising a response signal that is a function of a first data corresponding to a generator generating the response signal and a second data corresponding to a predetermined stimulus for generating the response signal, wherein the digital signature comprises binary data, wherein the response signal is a measurable response of the generator to the predetermined stimulus that is a function of change in electrical properties of resistance or impedance in the generator. wherein the generator generating the smell-related response signal is a Metal Oxide Semiconductor (MOS) in a sensor or a sensor pixel of a sensor array having a plurality of MOS sensor pixels having an MOS active material exposed to an analyte in the gas environment and the predetermined stimulus is a sequence of predetermined temperatures.

18 Claims, 14 Drawing Sheets
(1 of 14 Drawing Sheet(s) Filed in Color)

Acetaldehyde

Acetone

Scanned spectra

Signal strength

Sweeping steps
(Temperature °C)

(51) Int. Cl.
  *G06N 7/00* (2023.01)
  *G01N 33/00* (2006.01)
  *G06F 16/9035* (2019.01)

(58) Field of Classification Search
  USPC .......................................................... 707/741
  See application file for complete search history.

(56) References Cited

U.S. PATENT DOCUMENTS

| | | | |
|---|---|---|---|
| 2003/0136960 A1* | 7/2003 | Goodman | G01N 33/0031 257/40 |
| 2008/0077331 A1* | 3/2008 | Lewis | G01N 33/0075 702/30 |
| 2011/0172931 A1* | 7/2011 | Murthy | G16C 20/20 512/1 |
| 2013/0244336 A1* | 9/2013 | Mayer | G01N 33/0004 436/147 |
| 2015/0220199 A1 | 8/2015 | Wang et al. | |
| 2016/0051815 A1 | 2/2016 | Costanzo et al. | |
| 2018/0003660 A1* | 1/2018 | Tayebi | G01N 33/0047 |
| 2019/0369073 A1* | 12/2019 | Gafsou | G01N 33/0001 |
| 2020/0400631 A1* | 12/2020 | Gao | G06N 3/045 |
| 2021/0065273 A1* | 3/2021 | Amin | G06Q 30/0623 |

OTHER PUBLICATIONS

Microsoft Computer Dictionary, 5th Edition, Microsoft Corporation, Redmond, WA, © 2002, pp. 141 and 269-270.*
Brattoli, Magda, et al., "Odour Detection Methods: Olfactory and Chemical Sensors", Sensors 2011, vol. 11, May 16, 2011, pp. 5290-5322.*
Wilson, Alphus D., et al., "Applications and Advances in Electronic-Nose Technologies", Sensors 2009, vol. 9, Jun. 29, 2009, pp. 5099-5148.*
Karakaya, Diclehan, et al., "Electronic Nose and Its Applications: A Survey", International Journal of Automation and Computing, vol. 17, No. 2, Dec. 28, 2019, pp. 179-209.*
Nakamoto, Takamichi, et al., "Selection Method of Odor Components for Olfactory Display Using Mass Spectrum Database", IEEE Virtual Reality 2009, Lafayette, LA, Mar. 14-18, 2009, pp. 159-162.
Muller, Philipp, et al., "Indoor Localisation using Aroma Fingerprints: A First Sniff", WPNC 2017, Bremen, Germany, Oct. 25-26, 2017, 5 pages.
Dunkel, Mathias, et al., "Superscent—a database of flavors and scents", Nucleic Acids Research 2009, vol. 37, Database Issue, pp. D291-D294.

* cited by examiner

| Degree C | A1 | B1 | C1 |
|---|---|---|---|
| 200 | 50 | 0 | 67 |
| 210 | 75 | 22 | 33 |
| 220 | 100 | 87 | 67 |
| 230 | 225 | 174 | 133 |
| 240 | 375 | 217 | 333 |
| 250 | 425 | 261 | 500 |
| 260 | 525 | 304 | 533 |
| 270 | 700 | 435 | 400 |
| 280 | 800 | 500 | 267 |
| 290 | 900 | 522 | 233 |
| 300 | 950 | 435 | 800 |
| 310 | 1000 | 348 | 1000 |
| 320 | 1000 | 326 | 933 |
| 330 | 850 | 370 | 867 |
| 340 | 650 | 413 | 633 |
| 350 | 500 | 435 | 600 |
| 360 | 400 | 652 | 533 |
| 370 | 375 | 1000 | 567 |
| 380 | 400 | 1000 | 433 |
| 390 | 450 | 870 | 300 |
| 400 | 500 | 652 | 200 |
| 410 | 400 | 522 | 200 |
| 420 | 335 | 435 | 200 |
| 430 | 250 | 413 | 233 |
| 440 | 150 | 326 | 200 |
| 450 | 100 | 261 | 167 |
| 460 | 75 | 217 | 133 |
| 470 | 50 | 196 | 67 |
| 480 | 25 | 174 | 33 |
| 490 | 0 | 87 | 0 |

SYSTEMS AND METHODS FOR GENERATING SMELL DATA AND A DATABASE THEREOF

CROSS-REFERENCE TO RELATED APPLICATIONS

This application is a Continuation of U.S. patent application Ser. No. 17/007,292, filed on Aug. 31, 2020, the contents of which are incorporated herein in their entirety by reference.

TECHNICAL FIELD

The present invention generally relates to generation of a multi-dimensional odor or smell information for an analyte in a gaseous environment using Metal Oxide Semiconductor (MOS) sensor array by temperature sweeping or scanning for each metal oxide active material in a MOS sensor array and more particularly it relates to systems and methods for generating a structured database from response signals. i.e., towards a database structure, to generate multi-dimensional smell information for further use in smell related applications.

BACKGROUND

The term smell in the invention's context is different from the sense of smell by humans. Smell refers to any compound that vaporizes and it is those vaporized molecules that can diffuse in the air and can be detected by an organism or a man-made sensor. This means that the chemical molecule can go into a gaseous phase and then the scent or smell is detected by the sensor. The sensor or sensors may not necessarily be in direct contact with the source. Even though the source that generates the chemicals is not in contact with the sensor, the molecules or vapors generated can be detected and then the source can be localized by tracing the smell gradients i.e., by checking the signal's intensity. Typically, the closer the source is, the stronger the signals can be. This strategy is used by insects or in the animal kingdom, as they find the source of a smell by the smell gradients. Artificial olfactory systems, sometimes referred to as electronic noses, utilize an array of gas sensors to detect the concentrations of various gases being emitted by an object or composition. The aroma or scent or smell or odor of an item is typically unique to that item and serves as an olfactory fingerprint that can be used to identify that item. The smell of an item can be comprised of various gases mixed together in a unique combination. By exposing the smell of an item to a sensor array, the smell data is generated. Such smell data when structured into a smell information can be helpful in various fields for smell identification, monitoring, tracking, discovery, mapping etc. The testing of gases, volatile organic compounds (VOCs), and other airborne substances can be performed for a variety of reasons. One example is personalized health monitoring through breath analysis. Another example is pollution screening and/or monitoring. Yet other examples include environmental screening and/or monitoring, industrial process monitoring, and the like. A variety of sensors can be used to perform such testing to various degrees. Such sensors may vary in size, design, materials, and operation.

Commercial artificial olfactory systems are widely used by industry to provide quantifiable quality control parameters to aromatic products. For example, artificial olfactory systems are used by industry to identify if one batch of perfume smells the same as previous lots or if cheese has aged to the proper degree. With items such as perfume, wine and cheese that have strong aromas, the human nose is typically not sensitive enough to detect minor anomalies in the aromas from day to day. However, by using artificial olfactory systems, the aroma of these items can be quantified and scientifically analyzed. As such, minor anomalies can be detected, and a higher degree of quality control can be maintained. There exist many applications where the identification of items by an artificial olfactory system would be beneficial, however such applications may require identification on a scale of a few seconds rather than on a scale of a few minutes, thereby eliminating the use of traditional slow artificial olfactory systems. For example, in a grocery store, a customer may come to the cashier's counter with apples. The apples are not individually labeled, so it is difficult for the cashier to determine what type of apple is being bought. Since different types of apples have different prices, the cashier must determine the type of apple before the customer can pay for the apples. If an artificial olfactory system were available, the apples could be identified by their smell. However, such an artificial olfactory system would have to work rapidly and provide an identification in a matter of seconds. Another application for an artificial olfactory system with a rapid response time would be at airport baggage inspection stations. At such inspection stations, pieces of luggage could be inspected by their aroma, thereby providing a means of detecting illegal drugs, explosives, or other contraband. In such an application, the olfactory inspection would have to be completed in a matter of seconds for each piece of luggage.

For an efficient smell application system such as identification, monitoring etc., two things are important. One having a rich or fine fingerprint of smell information and two efficient organization or structuring of data for using Artificial Intelligence (AI) techniques for easy and better methods of comparison.

Reference patents, U.S. Pat. Nos. 10,422,771B2; 5,675,070A; 10,152,116B2; 6,895,338B2; and 8,726,719B2 disclose a system for identifying the odor or smell, however, the smell data that is generated is not based on temperature sweeping. The data generated from the above patents is not as rich as the data generated from a MOS sensor array by temperature sweeping. U.S. Pat. No. 6,494,077B2 discloses temperature sweeping data with respect to a sensor type. However, it does not disclose any smell database or smell data pattern formulation or any standardized database of known smells for the use of Artificial Intelligence (AI) or Mathematical technique or pattern recognition methods towards rapid smell identification applications. U.S. Pat. No. 10,330,624B2 discloses temperature sweeping with respect to a sensor type. However, it does not disclose any multi-dimensional structured smell information for smell data for various smell related applications.

Techniques and devices for detecting a wide variety of analytes in fluids such as vapors, gases and liquids are well known. Such devices generally comprise an array of sensors that in the presence of an analyte produce a unique output signature. Using pattern recognition algorithms, the output signature, such as an electrical response, can be correlated and compared to the known output signature of a particular analyte or mixture of Substances. By comparing the unknown signature with the stored or known signatures, the analyte can be detected, identified, and quantified. Examples of such detection devices can be found in U.S. Pat. Nos. 5,571,401; 5,675,070; 5,697,326; 5,788,833; 5,807,701; and 5,891,398, however they are based on individual profiles or signatures of the smell data from each of the sensors. None of them disclose any structure for a database that is to be used for efficient use of pattern recognition or machine learning or image processing or Artificial Intelligence (AI) or mathematical methods.

Generally, most of the techniques rely upon a predetermined pattern recognition algorithm to analyze data to compare a known individual signature with an unknown individual signature to detect and identify an unknown analyte. These techniques, however, are often cumbersome and time consuming especially when the database corresponds to big data. Many methods also require highly manual data processing techniques. Additionally, each algorithm must often require manual input to be used with the known signature. Furthermore, there are many different types of algorithms, which must often be used. These different algorithms are often incompatible with each other and cannot be used in a seamless and cost-effective manner. In order for the smell applications such as identifying, monitoring, discovering, tracking or mapping of smell, to be efficiently implemented, it is to be realized that the individual response signal from each sensor pixel has to be organized or structured in an efficient way for generating a structured database of smell data so that the comparison or correlation of the input smell data with a standards smell information stored in a central database can be rapidly and quickly processed.

Structured data is highly organized and easily understood by machine language. It is organized in such a way that it is easily searchable in relational databases. Unstructured data has no pre-defined format or organization, making it much more difficult to collect, process, and analyze. With a structured database, input, search, and manipulation of structured data can be performed relatively quickly. This is the most attractive feature of structured data. Common examples of structured data are Excel files or Structured Query Language (SQL) databases. SQL, a Structured Query Language, is a domain-specific language used in programming and designed for managing data held in a relational database management system (RDBMS), or for stream processing in a relational data stream management system (RDSMS). It is particularly useful in handling structured data, i.e., data incorporating relations among entities and variables. SQL offers three main advantages over read-write Application Programme Interphases (APIs) such as Indexed Sequential Access Method (ISAM) or Virtual Storage Access Method (VSAM). Firstly, it introduced the concept of accessing many records with one single command. Secondly, it eliminates the need to specify how to reach a record, e.g., with or without an index. Finally, SQL uses a human-readable syntax that allows users to be quickly productive without a requirement for long-term, technical training.

Metal oxide sensors are temperature dependent. Temperature sweeping is the most unique part of the U.S. Pat. No. 10,330,624B2 technology and the advantage of doing the temperature sweep is to create another dimension of information that is not existing in other sensor systems. MOS sensor array creates much data from one particular pixel or metal oxide by temperature sweeping. Since multiple metal oxide pixels are present in one sensor array, multiple response signals are created when the sensor is used once. Other sensors or other methods that use metal oxide will not be able to create such rich data without temperature sweeping, particularly fine step sweeping. With lots of data that is available from such a MOS sensor array, rich information from the sensors can be created provided that the data is structured and organized efficiently.

Accordingly, a need therefore exists for systems and methods for generating multi-dimensional structured smell information from smell data produced by metal oxide semiconductor (MOS) sensor array by temperature sweeping of each sensor material.

SUMMARY

A database comprising a digital signature of a smell, the digital signature comprising a smell data, the smell data comprising a response signal that is a function of a first data corresponding to a generator generating the response signal and a second data corresponding to a predetermined stimulus for generating the response signal; wherein the digital signature comprises binary data; wherein the response signal is a measurable response of the generator to the predetermined stimulus that is a function of change in electrical properties of resistance or impedance in the generator.

A database comprising, a digital signature of a smell comprising a smell data, wherein the smell data comprises a response signal that is a function of a first data corresponding to a material type (generator) generating the response signal and a second data corresponding to a predetermined stimulus for generating the response signal; a smell condition data associated with the smell data, wherein the smell condition data comprises a condition under which the response signal was generated; and an index for the smell data; wherein the smell data is stored in a data structure on a computer readable storage medium that is associated with a computer executable program code; wherein the data structure comprises the smell data arranged in a computer-readable matrix or heat-map format; and wherein the response signal is a measurable response of the generator to the predetermined stimulus that is a function of change in electrical properties of resistance or impedance in the generator.

A system comprising a sensor and a database, the database comprising, a digital signature of a smell comprising a smell data, wherein the smell data comprises a response signal that is a function of a first data corresponding to a material (generator) type generating the response signal and a second data corresponding to a predetermined stimulus for generating the response signal; a smell condition data associated with the smell data, wherein the smell condition data comprises a condition under which the smell data was generated; and an index for the smell data; wherein the smell data is stored in a data structure on a computer readable storage medium that is associated with a computer executable program code; wherein the data structure comprises the smell data arranged in a computer-readable matrix or heat-map format; and wherein the response signal is a measurable response of the generator to the predetermined stimulus that is a function of change in electrical properties of resistance or impedance in the generator.

A method comprising creating and using a database, the database comprising, a digital signature of a smell comprising a smell data, wherein the smell data comprises a response signal that is a function of a first data corresponding to a material type (generator) generating the response signal and a second data corresponding to a predetermined stimulus for generating the response signal; a smell condition data associated with the smell data, wherein the smell condition data comprises a condition under which the smell data was generated; and an index for the smell data; wherein the smell data is stored in a data structure on a computer readable storage medium that is associated with a computer executable program code; and wherein the data structure comprises the smell data arranged in a computer-readable matrix or heat-map format; and wherein the response signal is a measurable response of the generator to the predetermined stimulus that is a function of change in electrical properties of resistance or impedance in the generator.

BRIEF DISCUSSION OF THE DRAWINGS

The patent or application file contains at least one drawing executed in color. Copies of this patent or patent application publication with color drawing(s) will be provided by the Office upon request and payment of the necessary fee.

In the present disclosure, reference is made to the accompanying drawings, which form a part hereof. In the drawings, similar symbols typically identify similar components, unless context dictates otherwise. Various embodiments described in the detailed description, drawings, and claims are illustrative and not meant to be limiting. Other embodiments may be used, and other changes may be made, without departing from the spirit or scope of the subject matter presented herein. It will be understood that the aspects of the present disclosure, as generally described herein, and illustrated in the Figures, can be arranged, substituted, combined, separated, and designed in a wide variety of different configurations, all of which are contemplated herein.

REFERENCES

Figure 1:
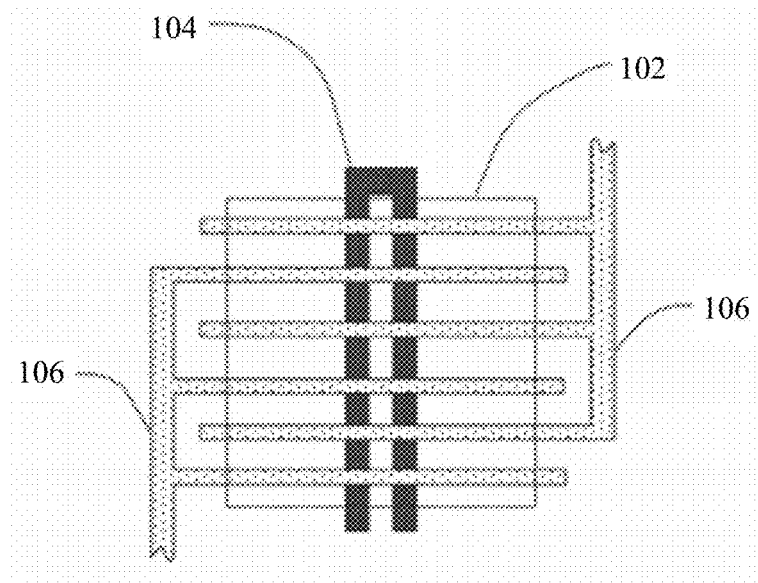
FIG. 1 is a schematic view of a Metal Oxide Semiconductor (MOS) sensor pixel in accordance with an invention embodiment.

All patents, patent application publications, and non-patent literature mentioned in the application are incorporated by reference in their entirety.

DETAILED DESCRIPTION

Although the following detailed description contains many specifics for the purpose of illustration, a person of ordinary skill in the art will appreciate that many variations and alterations to the following details can be made and are considered to be included herein.

Accordingly, the following embodiments are set forth without any loss of generality to, and without imposing limitations upon, any claims set forth. It is also to be understood that the terminology used herein is for the purpose of describing particular embodiments only and is not intended to be limiting. Unless defined otherwise, all technical and scientific terms used herein have the same meaning as commonly understood by one of ordinary skill in the art to which this disclosure belongs.

As used in this written description, the singular forms "a," "an" and "the" include express support for plural referents unless the context clearly dictates otherwise. Thus, for example, reference to "a sensor" includes a plurality of such sensors.

In this disclosure, "comprises," "comprising," "containing" and "having" and the like can have the meaning ascribed to them in U.S. patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. patent law. "Consisting essentially of" or "consists essentially of" have the meaning generally ascribed to them by U.S. patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open-ended term in this written description, like "comprising" or "including," it is understood that direct support should also be afforded to "consisting essentially of" language as well as "consisting of" language as if stated explicitly and vice versa.

"The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. Occurrences of the phrase "in one embodiment," or "in one aspect," herein do not necessarily all refer to the same embodiment or aspect.

As used herein, the term "analyte" refers to any molecule, compound, substance, agent, material, etc., for which detection is sought. In one aspect, an "analyte" may be capable of detection by a MOS sensor. In another aspect, an "analyte" can be capable of reacting with, and thus creating a detectable change in, a MOS active material. In some circumstances an "analyte" can be present in a gas environment. Non-limiting examples can include gases, airborne inorganic molecules, airborne organic molecules, volatile organic compounds, airborne particulate matter, vapors, vaporized solid or liquid and the like, including combinations thereof.

As used herein, "enhanced," "improved," "performance-enhanced," "upgraded," and the like, when used in connection with the description of a device or process, refers to a characteristic of the device or process that provides measurably better form or function as compared to previously known devices or processes. This applies both to the form and function of individual components in a device or process, as well as to such devices or processes as a whole.

As used herein, "coupled" refers to a relationship of electrical or physical connection or attachment between one item and another item and includes relationships of either direct or indirect connection or attachment. Any number of items can be coupled, such as materials, components, structures, layers, devices, objects, etc.

As used herein, "directly coupled" refers to a relationship of electrical or physical connection or attachment between one item and another item where the items have at least one point of direct physical contact or otherwise touch one another. For example, when one layer of material is deposited on or against another layer of material, the layers can be said to be directly coupled.

Objects or structures described herein as being "adjacent to" each other may be in physical contact with each other, in close proximity to each other, or in the same general region or area as each other, as appropriate for the context in which the phrase is used.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such an item as long as there is no measurable effect thereof.

As used herein, the term "about" is used to provide flexibility to a numerical range endpoint by providing that a given value may be "a little above" or "a little below" the endpoint. However, it is to be understood that even when the term "about" is used in the present specification in connection with a specific numerical value, that support for the exact numerical value recited apart from the "about" terminology is also provided.

As used herein, a plurality of items, structural elements, compositional elements, and/or materials may be presented in a common list for convenience. However, these lists should be construed as though each member of the list is individually identified as a separate and unique member. Thus, no individual member of such a list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range, or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

As used herein, a sensor refers to a generic term, it can be a different type of sensor and have different structure. Generally, a sensor is a device comprising a sensing unit, such as a sensor array, and a control circuitry or an electronic processing unit (a processor). A sensor array refers to a sensing unit having different sensing elements or pixels on a single substrate or in a single device. A sensor pixel refers to an element of a sensor or a sensor array. As a sensor pixel is the essential element of a sensor, the terms "sensor" and "sensor pixel" may be interchangeable and its exact meaning depends on the context.

As used herein, dimension is a data variable or set composed of individual, non-overlapping data elements. As an example, a multi-dimensional smell data comprises type of MOS sensor pixel as one dimension, temperature as another dimension, response of MOS sensor pixel as another dimension, source of smell as another, date and time of smell generated as another dimension etc. Additional data elements form additional dimensions.

As used herein, "multi-dimensional" is not referring to geometric dimension but a virtual property in which a material is characterized using two or more means that are physically or chemically unrelated. For example, information of a VOC measured with different metal oxide semiconductor (MOS) materials is considered to be in one dimension; information of the same VOC measured by a MOS material at different temperature settings is considered to be in another dimension. Thus, information for the same VOC is considered to be two dimensional when the information is obtained using different MOS materials as well as under different temperatures. A multi-dimensional smell data when organized or structured forms a multi-dimensional smell information.

As used herein, a response signal is a measurable response of the sensing element or MOS pixel in a sensor, including changes in electrical properties (resistance/impedance). It is an analog signal, convertible and recordable in digital forms. The unit of a response signal is typically a resistance (R) ratio. For example, Rg/Ra, where "R" is the MOS active material's resistance at a given temperature; "Rg" indicates the resistance when the sensor is exposed to a target gas (VOC); "Ra" is the resistance when the pixel is exposed to air (for baseline information). Ra/Rg can also be used depending on the MOS material type (N-type or P-type).

As used here in, a generator is a sensor pixel of a sensor array, or a MOS active material exposed to an analyte in a gas environment and is capable of generating a response signal.

As used herein, a predetermined stimulus is an input stimulus provided to a sensor in order to measure its response that corresponds to the predetermined stimulus, herein it is a sequence of predetermined temperatures.

As used herein, a smell data is an array comprising response signals of a plurality of MOS sensor pixel at a plurality of predetermined temperatures wherein the plurality of MOS pixels is a vector and the plurality of predetermined temperatures is another vector, wherein the vector is defined as a one-dimensional array used for storing values.

As used herein, a digital signature of smell comprises differing responses across the MOS sensor pixels at a plurality of predetermined temperatures in an array which can be used as a type of "fingerprint" or digital fingerprint or digital signature or pattern to selectively distinguish between analytes that are indistinguishable or difficult to distinguish by the response characteristics of individual MOS sensor pixels alone.

As used herein, a smell database comprises digital signature of plurality of smells and is a relational database. Various database operations which vehicles through which users and applications have access to data in a relational database can be performed on the smell database.

As used herein, a heatmap or heat map is a data visualization technique that shows magnitude of a phenomenon as color in two dimensions, depicting values for a main variable of interest across two axis variables as a grid of colored squares. The axis variables are divided into ranges like a bar chart or histogram, and each cell's color indicates the value of the main variable in the corresponding cell range. The variation in color may be by hue or intensity, giving obvious visual cues about how the phenomenon is clustered or varies over space.

Implementations and all of the functional operations described in this specification may be realized in digital electronic circuitry, or in computer software, firmware, or hardware, including the structures disclosed in this specification and their structural equivalents, or in combinations of one or more of them. Implementations may be realized as one or more computer program products, i.e., one or more modules of computer program instructions encoded on a computer readable medium for execution by, or to control the operation of, data processing apparatus. The computer readable medium may be a machine-readable storage device, a machine-readable storage substrate, a memory device, a composition of matter effecting a machine-readable propagated signal, or a combination of one or more of them. The term "computing system" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

A computer program (also known as a program, software, software application, script, or code) may be written in any appropriate form of programming language, including compiled or interpreted languages, and it may be deployed in any appropriate form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, for example without limitation, a PLC (Programmable Logic Controller), an FPGA (field programmable gate array), an ASIC (application specific integrated circuit), Program-specific Standard Products (ASSPs), System-on-a-chip systems (SOCs), Complex Programmable Logic Devices (CPLDs), etc.

Processors suitable for the execution of a computer program include, by way of example, both general and special purpose microprocessors, and any one or more processors of any appropriate kind of digital computer. Generally, a processor will receive instructions and data from a read only memory or a random access memory or both. Elements of a computer can include a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media, and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

To provide for interaction with a user, implementations may be realized on a computer having a display device, e.g., a CRT (cathode ray tube) or LCD (liquid crystal display) monitor, for displaying information to the user and a keyboard and a pointing device, e.g., a mouse or a trackball, by which the user may provide input to the computer. Other kinds of devices may be used to provide for interaction with a user as well; for example, feedback provided to the user may be any appropriate form of sensory feedback, e.g., visual feedback, auditory feedback, or tactile feedback; and input from the user may be received in any appropriate form, including acoustic, speech, or tactile input.

Implementations may be realized in a computing system that includes a back end component, e.g., as a data server, or that includes a middleware component, e.g., an application server, or that includes a front end component, e.g., a client computer having a graphical user interface or a Web browser through which a user may interact with an implementation, or any appropriate combination of one or more such back end, middleware, or front end components. The components of the system may be interconnected by any appropriate form or medium of digital data communication, e.g., a communication network. Examples of communication networks include a local area network ("LAN") and a wide area network ("WAN"), e.g., the Internet.

The computing system may include clients and servers. A client and server are generally remote from each other and typically interact through a communication network. The relationship of client and server arises by virtue of computer programs running on the respective computers and having a client-server relationship to each other.

Embodiments of the present invention may comprise or utilize a special purpose or general-purpose computer including computer hardware. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media and transmission computer-readable media.

Physical computer-readable storage media includes RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network, such as a 5G network, or another communications connection (either hardwired, wireless, or a combination of hardwired or wireless) to a computer, the computer properly views the connection as a transmission medium. Transmission media can include a network and/or data links which can be used to carry data or desired program code means in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

Even though particular combinations of features are recited in the claims and/or disclosed in the specification, these combinations are not intended to limit the disclosure of possible implementations. Other implementations are within the scope of the following claims. For example, the actions recited in the claims may be performed in a different order and still achieve desirable results. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

Further, the methods may be practiced by a computer system including one or more processors and computer-readable media such as computer memory. In particular, the computer memory may store computer-executable instructions that when executed by one or more processors cause various functions to be performed, such as the acts recited in the embodiments.

An initial overview of technology embodiments is provided below, and specific technology embodiments are then described in further detail. This initial summary is intended to aid readers in understanding the technology more quickly but is not intended to identify key or essential technological features, nor is it intended to limit the scope of the claimed subject matter.

The embodiments herein and the various features and advantageous details thereof are explained more fully with reference to the non-limiting embodiments that are illustrated in the accompanying drawings and detailed in the following description.

Current invention relates to systems and methods for generating multi-dimensional structured smell information from smell data produced by metal oxide semiconductor (MOS) sensor array by temperature sweeping of each sensor material in a computer readable format. In this disclosure, temperature sweeping, and temperature scanning are used interchangeably.

It is important to understand the structure of Metal Oxide Semiconductors (MOS) sensors which sense the smell or odor and their arrangement. The MOS sensor array comprises a plurality of sensing components referred to as pixels and these pixels are arranged geometrically in two dimensions as a first vector and a second vector to make up a sensor array or MOS Sensor. MOS sensors are scalable by adding or deleting the pixels. When the sensor is exposed to Volatile Organic Compounds (VOCs) the response of each of the pixels of the MOS sensor array creates another dimension of data, which is obtained by doing the temperature sweeping, on top of the physical or geometrical two dimensions. With all the smell data generated, the next critical question is how to organize this generated data and utilize it to create smell information. Data is a collection of individual numbers that contain raw values which does not necessarily carry any specific meaning. Data is unorganized raw facts that need processing without which it is seemingly random and useless to humans. Information depends on data and is a group of data that collectively carries a logical meaning. Information is a processed, organized data presented in a given context and is useful to humans. People just looking at the data will not be useful, but information created from the data is useful. Information is specific to the expectations and requirements because it is well organized and all the irrelevant and unnecessary facts, if any, are removed during the transformation process.

The following paragraphs explain the configuration and construction of the MOS sensor array and generating the data through temperature sweeping.

Gas sensors, including VOC sensors, are based on various different principles. For example, a sensor may employ electrochemistry, optical absorption, photo-ionization, enzymatic reaction, metal oxides, resistive-change techniques, and other techniques. Such sensors are typically difficult to miniaturize. For example, electrochemical sensors employ double layer capacitance, which becomes dominant at small scales and impedes sensitivity. Additionally, optical sensors may require bulky components and may have high power requirements. Miniaturized standalone MOS-based gas sensors can have several problems that limit the use of these devices. As one example, due to analyte cross-sensitivity quantitative analysis of an analyte (e.g., measuring concentration) is difficult. While various modifications to MOS sensor designs, such as doping for example, can reduce these problems, analyte cross-sensitivity and consequent lack of selectivity still remains. As another example, changing the operational temperature of a MOS sensor can provide enhanced partial selectivity for a given analyte over a different given analyte. Additionally, environmental conditions can impact the sensitivity of most MOS materials and may lead to erroneous readings due to the lack of proper calibration. One non-limiting example of such an environmental condition is humidity.

Invention aspects relate to devices and systems having a low power, high sensitivity array of MOS sensor pixels that can simultaneously and selectively detect chemical reactions involving one or more analytes and a reactant, such as adsorbed oxygen molecules, at the MOS active materials of the sensor pixels. Such reactions cause changes in the electrical resistance of the MOS active material, thereby providing accurate concentrations of the analyte or analytes. In one aspect, the MOS sensor pixel array is portable and is for use as a field instrument. In another aspect, the MOS sensor array may be used in a laboratory setting. An MOS sensor array may be composed of a plurality of components for sensing where each of the components may be referred to as a pixel or sensor pixel. Pixels or sensor pixels may be composed of different MOS active materials within the same array. These various different MOS active materials can be sensitive and/or selective to a specific gas, VOC, or a group of gases and VOCs.

More specifically, in one aspect an array of MOS-based sensor pixels is presented that is selective and can provide single or multiple analyte selectivity including, in some aspects, concentration measurements for single and/or multiple analytes. In one aspect, a MOS pixel is heated to a sequence of different predetermined temperatures via a heating element. The different predetermined temperatures may represent a range of temperatures to which the MOS pixel is heated for a period of time and includes specific individual temperatures within the time period (e.g., a number of specific temperatures in the range are each achieved and held for a specified time). In some aspects, this may be described as fine-temperature scanning. A response signal is then detected via an electrode. A different response signal may be detected at each of the predetermined temperatures, or other determined increments within the temperature range. The response signals are then assembled into sample data. For example, a data set may comprise more than 5 data points or more than 10 data points. In one example, a data set may comprise from 2 to 400 data points. In one aspect, the sample data set is represented or potentially (virtually) represented graphically by a graph that displays a spectrum of a data set with at least one peak. This may be described as a graphic spectrum. In one embodiment, the data points may be plotted in the spectrum as a function of temperature with a spectrum or profile formed by connecting the data points from one end of the temperature range to the other. It should be appreciated that the sample data is not limited to a graphic spectrum or a spectrum with peaks and may be a set of data that is used to extract the features for machine learning and identifying an analyte. The sample data is then compared to standards data in a standards database to identify the analyte. The comparison may include graphic comparison, mathematical de-convolution, statistical analysis, etc.

The sample data can also be assembled from multiple identical sensor pixels, each operating at different temperature ranges where the different temperature ranges may be continuous with one another. For example, a first temperature range may be 200-300 degrees Celsius (° C.) (e.g., 200-300° C.) where first MOS sensor pixel for a MOS sensor operates and where a second temperature range is 300-400° C. (e.g., 300-400° C.) where a second MOS sensor pixel for the same MOS sensor operates simultaneous with the first MOS sensor pixel. Collection of such sample data generated by the first and second sensor pixels operating simultaneously in different temperature ranges can shorten the detection time. The sample data may also be employed to determine a concentration of the analyte. In one aspect, the peak in the spectrum is used to identify the analyte. For example, each unique analyte may have a different peak in a spectrum of data.

Although Fine-Step-Temperature-Sweeping (FSTS) can potentially generate information that helps resolve VOC identities, it demands for long response time, which is not desirable to mobile applications. To reduce response time while retaining the capability of VOC identification, the concept of Temperature-Dependent Resistance Spectrum (TDRS) reconstruction after sub-range Fine-Step-Temperature-Sweeping (FSTS) by redundant sensor pixels.

Pixel calibration: Before used for TDRS reconstruction, redundant pixels will be examined and calibrated for baseline. Ideally, each of the redundant pixels is used for full range FSTS and their TDRSs are compared. If they generate the same TDRSs for a given VOC, these pixels can be used after adjusting their baselines. Those giving different signatures should be treated as outliers and not be used.

Sub-range FSTS test: Multiple pixels of the same MOS in a sensor array will be used to perform sub-range FSTS. For example, when 4 pixels are used, each covering a range of 50° C., only about 25 s are needed to collect as much information as that collected by 1 pixel for 100 s. When 8 pixels are used, the scan time can be reduced to 12.5 s. The response time can be potentially reduced to <10 s when more than 10 pixels are used.

TDRS reconstruction validation: It is anticipated that a reconstructed TDRS is comparable to that from a full range FSTS. However, reconstruction would not be possible if a MOS pixel needs to be pre-conditioned and its response is temperature-dependent. For example, if a lower temperature that a pixel has experienced would affect the performance of the same pixel in a higher temperature, or vice versa (temperature-conditioning effect), TDRS would not be reliably reconstructed. Eliminating the possibility of temperature-conditioning effect is critical to mobile VOC sensing that is based on MOS technology. These steps are designed to reduce risks in VOC profiling and response time reduction.

Moreover, different MOS active materials can be sensitive to different analytes, as well as have different sensitivities to the same analyte, and can thus be utilized to generate specific analyte selectivity. As such, by utilizing individual MOS sensor pixel heating, different MOS active materials, and/or other techniques for tuning individual MOS sensor pixels, arrays having high selectivity for one or more analytes can be designed and implemented. In one aspect, different pixels or different portions of pixels may be heated to different temperatures, or though different temperature ranges, relative to other pixels within the same array simultaneously. Alternatively, all pixels in an array can be heated to the same temperature or same range of temperatures simultaneously. The different pixels may be composed of the same MOS active material but heated to different temperatures simultaneously in order to detect response signals from the analyte in a more efficient manner. In one aspect, the response signal is based on a change in electrical resistance of a MOS active material (i.e., the sensing layer) as a result of an interaction with an analyte. Once in contact with the analyte, the change in resistance of the MOS film can be detected.

Various MOS sensor designs are contemplated that can be utilized in the implementation of various invention embodiments, and such sensor designs can vary depending on a variety of factors, including the preferences of the designer or user of a given sensing device. The scope of the present disclosure is not limited, therefore, to any specific MOS sensor design.

Generally, a MOS sensor array can include a MOS active or sensing material and a heating element to heat the MOS active material to a temperature, or range of temperatures, at which analyte detection is performed. Various additional components can also be included in a MOS sensor, such as temperature sensors, environmental sensors, electrodes, readout circuitry, and the like. A given sensor array can have all MOS sensors of the same design and having the same sensor components, or the sensor array can have different MOS sensor designs and/or components across the array.

One non-limiting example of a MOS sensor pixel is shown in FIG. 1. The sensor pixel can include a MOS active material 102 positioned to be exposed to a sample to be tested. Note that the MOS active material 102 is shown as a transparent layer in FIGS. 1 and 2 to allow the underlying structures to be more clearly shown. A heating element 104 is thermally coupled to the MOS active material 102 and is positioned to facilitate heating of the MOS active material. In some embodiments, heating element geometry may be specifically configured in order to lower or minimize power consumption, lower, or minimize heat dissipation, or provide uniform heating. In some embodiments, more than one such advantage can be obtained with a single heating element geometry or configuration. The device can further include one or more electrodes 106 to provide further functionality. For example, in one aspect the electrode 106 can receive and transmit signals generated in the MOS active material. In some cases, a reaction between the MOS active material and an analyte result in a resistance change that can be detected by the electrode. In addition to analyte-related signals (including signals indicating the absence of an analyte), the electrode can receive and transmit signals relating to analyte concentration, the temporal fluctuations in analyte level, as well as signals from other components or modules of the device. Advantageously, in some embodiments, the geometry or configuration of the electrode can be specifically selected to increase or otherwise maximize sensitivity to resistance change in the MOS, and/or to fit a resistance range that is compatible with a readout circuit.

In one aspect, active areas of the MOS sensor, including the sensor pixels, MOS materials, electrodes, etc., are designed on a suspended membrane where the suspended membrane is used to reduce heat dissipation and power consumption. This may be especially useful for portable or wearable application of MOS sensors. In one aspect, the suspended membrane is designed as thin as possible. In one aspect, the power consumption of an MOS sensor is reduced to below one watt (W). In one aspect, the power consumption of an MOS sensor is reduced to below one µW.

Figure 2:
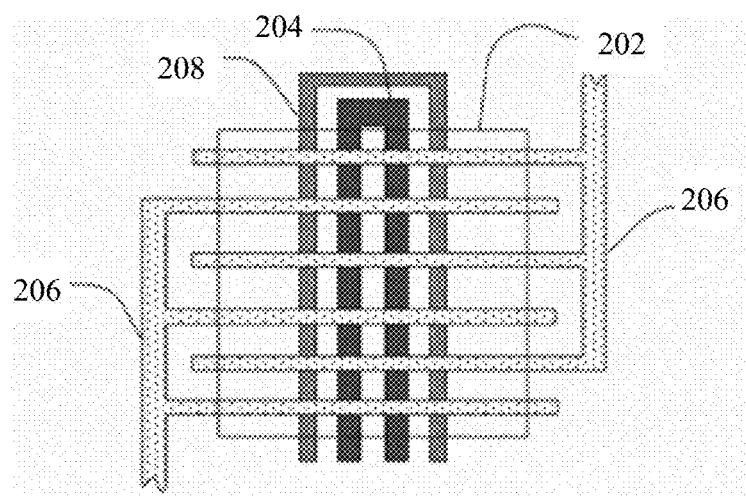
FIG. 2 is a schematic view of a MOS sensor pixel in accordance with an invention embodiment.

FIG. 2 shows another non-limiting example of a MOS sensor pixel including a MOS active material 202 positioned to be exposed to a sample to be tested and a heating element 204 thermally coupled to the MOS active material 202 and positioned to facilitate heating of the MOS active material. The device includes one or more electrodes 206, and a temperature sensor 208 thermally coupled to the MOS active material 202. The temperature sensor can thus detect and/or monitor the temperature of the MOS active material. In some cases, the temperature sensor can detect and report heating conditions generated by the heating element so that the heating of the MOS can be controlled, tuned, or otherwise optimized for a given application. If local temperature were to drift due to thermal fatigue or non-homogeneous dissipation mechanisms (presence of convection and/or radiation), for example, the uniform heating of the MOS active material would be affected, thus disrupting precise and reproducible temperatures. By reading the temperature at the MOS active material and being able to control it precisely, the detection sensitivity of the sensor can be more accurately ascertained, particularly for sensors having a temperature-dependent selectivity to a particular analyte or group of analytes. The temperature sensor can transmit signals to and from the sensor via one or more dedicated electrical channels, or via a shared electrical channel such as the electrode or other electrically useful connection.

In another aspect, a plurality of MOS sensors or sensor pixels is included in an array to provide selectivity to one or more analytes or groups of analytes. Additionally, such an array can provide effective identification and quantification of complex samples of related or unrelated analyte mixtures. For arrays having a size of three or more, MOS sensor pixel arrangements can be in a linear or in a two-dimensional array pattern. A given array can include at least two MOS sensor pixels, where each MOS sensor pixel has the same, similar, or different analyte selectivity as compared to other MOS sensor pixels in the array. In one aspect, a MOS sensor pixel array can selectively detect at least two analytes. In some cases, each of the MOS sensor pixels in an array can be selective to the same or different analytes. In other cases, one or more MOS sensor pixels in an array can be selective to a single given analyte or multiple analytes. As one example, half of the MOS sensor pixels in an array can be selective to one analyte, while the other half of the MOS sensor pixels can be selective to another analyte. In another example, multiple groups of MOS sensor pixels can be included in an array, where each group is selective to a different analyte or group of analytes.

Furthermore, in some cases the individual pixels of the MOS sensor of an array may not be selective to a specific analyte or analytes, and analyte selectivity of the array is a result of the pattern of partial or cumulative responses generated by the array as a whole. In other words, a plurality of MOS sensor pixels can be used as a collective to generate such selectivity. In some embodiments, the individual MOS sensor pixels in the array are not sufficiently selective to distinguish between multiple analytes by themselves. In additional embodiments, the MOS sensor pixels may have differing response characteristics to an analyte in a sample. The differing responses across the MOS sensor pixels in the array can be used as a type of "fingerprint" or digital fingerprint or digital signature or pattern to selectively distinguish between analytes that are indistinguishable or difficult to distinguish by the response characteristics of individual MOS sensor pixels alone. Once a pattern (e.g., a pattern of data peaks) for an analyte or a mixture of analytes is established, the response of the array to a sample can be compared to that pattern to determine if the analyte or mixture of analytes is present. This pattern recognition process can be used to selectively distinguish a single analyte, a few analytes, as well as complex mixtures of analytes in a sample. While the detection of an analyte or analytes can be dependent on matching a known response pattern or peak to the response of the array, in some cases statistical or other pattern recognition techniques can be employed to selectively detect one or more analytes to which a response pattern is not known. For example, the identity of a mixture of analytes in a sample can be extrapolated from known response patterns of the array to other analytes or mixtures of analytes.

The technique of using fingerprints, peaks, or patterns to selectively distinguish between analytes may rely upon one or more discrete temperature measurements. In one aspect, multiple discrete temperature measurements over a temperature range may generate response signals with spectroscopy-like signatures. For example, fine-temperature scanning of the analyte using the MOS sensor pixels can provide such response signals and related data. Such temperature scanning may be performed at predetermined temperatures. For example, a range of temperatures may be scanned where a given MOS sensor pixel is heated by a heating element to a first temperature for a period of time and is then heated to a second temperature for a period of time. The difference between the first and second temperature may be referred to as an interval, gap, increment, or resolution. Exemplary intervals may be 0.5, 1, 5, 10, or 20° C. or any other interval. As the intervals are moved closer together, the resultant data becomes more sensitive (not necessarily more sensitive but more informative or selective). In one embodiment, a MOS sensor pixel may scan through an entire range of temperatures sampling data at intervals. The range of temperatures scanned through may be any range of temperatures and may depend upon the type of analyte a sensor is designed to identify. In one embodiment, multiple identical MOS sensor pixels may scan through multiple temperature ranges sampling data at intervals, which collectively may scan through an entire temperature range which collectively assemble sampling data for the spectroscopy-like signatures. This is to reduce the detection time. In one embodiment, a sensor array may be programmed to change a range of temperatures to be scanned and may also change the period of time each temperature is sampled and may also change the intervals or resolution. In one aspect, a MOS sensor array can scan a temperature range of 200 to 400° C. In one aspect, a temperature range may not exceed an upper temperature where most VOCs will turn into $CO_2$. For example, a MOS sensor may not scan temperatures above 500 or 600° C. In one aspect, after a MOS sensor has identified an analyte, and it has been determined that sampling for such an analyte is complete, an MOS sensor pixel may undergo a cleaning cycle to clean the MOS sensor pixel so that it is ready to be exposed to a different analyte. For example, the cleaning cycle may be to heat the MOS sensor pixel to a high temperature such as a temperature exceeding 400 or 500° C.

In one aspect, the heating element heats the MOS active material to a sequence of predetermined temperatures. The sequence of predetermined temperatures may be a series of temperatures in a range of temperatures separated by equal or varied intervals. For example, the range of temperatures may be 200-400° C. with intervals of 5° C. so that the predetermined sequence of temperatures is 200, 205, 210, 215, 220 all the way up to 400. In one aspect, the heating element only requires a few milliseconds to heat the MOS sensor pixel to a predetermined temperature. However, the MOS sensor may require a few seconds to generate the response signals at the predetermined temperature. Therefore, the heating element may heat the MOS sensor pixel to a predetermined temperature for a predetermined period of time such as 2-5 seconds. This predetermined period of time can allow the analyte to interact with the MOS active material.

Furthermore, pattern recognition processes can be utilized in an array having analyte-selective MOS sensor pixels. In some cases, for example, a portion of an array can include analyte-selective MOS sensors, and another portion can include analyte-nonselective MOS sensor pixels that utilize pattern recognition for analyte detection.

Additionally, in some cases a pattern recognition process can be applied to the response patterns of analyte-selective MOS sensor pixels to detect unknown analytes, analyte mixtures, or analyte mixture concentrations.

Figure 3:
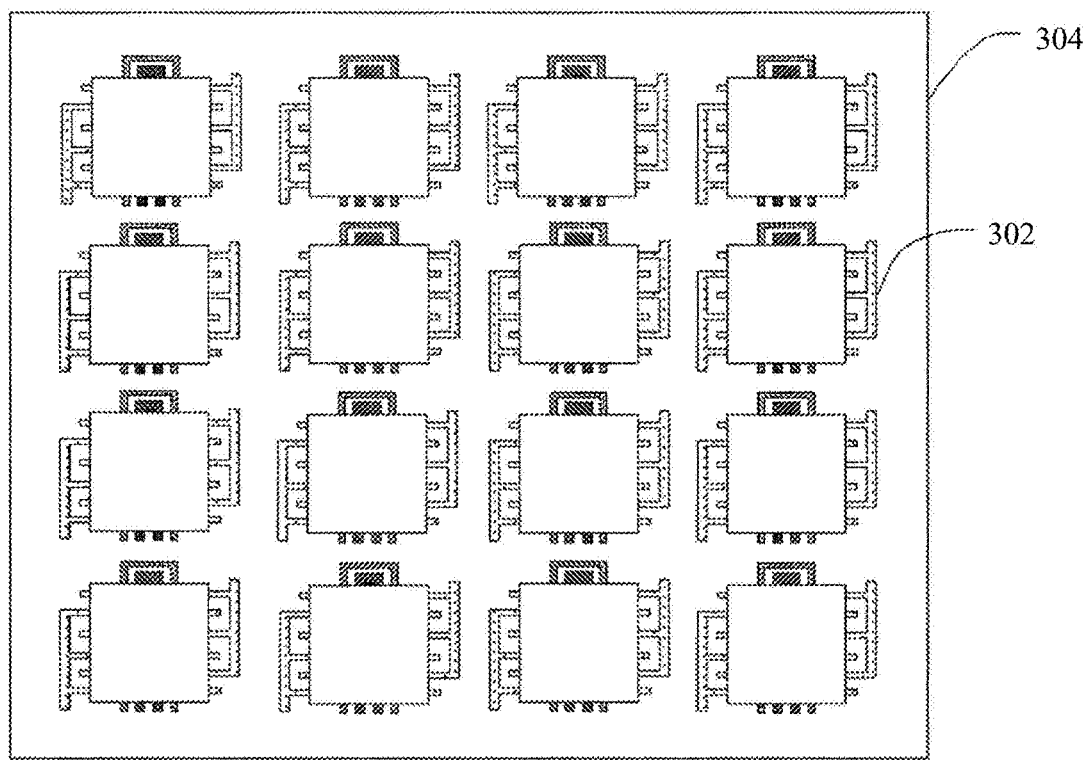
FIG. 3 is a schematic view of a MOS sensor array in accordance with an invention embodiment.

One non-limiting example of a MOS sensor pixel array is shown in FIG. 3, where 16 MOS sensor pixels 302 are arranged into a four-by-four grid on a support substrate 304. It is to be noted that connections to and from the MOS sensor pixels are not shown. While there is no limit to the number of MOS sensor pixels included in an array, in some aspects the array can include at least four MOS sensor pixels. In other aspects, the array can include at least 16 MOS sensor pixels. In yet other aspects, the array can include at least 24 MOS sensor pixels. In further aspects, the array can include at least 64 MOS sensor pixels. In yet further aspects, the array can include at least 256 MOS sensor pixels. However, the array can be in any format comprising of any number of pixels odd or even. In one aspect, the sensors in the array are co-fabricated with one another. It should be appreciated that the pixels of a sensor within the array may be each composed of the same MOS active materials or different materials. For example, a portion of the sensor pixels may be composed of a first MOS active material and a different portion of the sensor pixels may be composed of a second MOS active material.

Each MOS sensor pixel in an array can include a MOS active material and a heating element thermally coupled to the MOS active material in a position and orientation to facilitate heating of the MOS active material. One or more temperature sensors can additionally be included in the array. A temperature sensor can be integrated into each MOS sensor pixel as described above, or a temperature sensor can be incorporated at the array level to sense and monitor temperature across a region of multiple MOS sensor pixels. The MOS sensor pixels in the array may be spaced far enough apart so that a given MOS sensor pixel does not cross heat a different MOS sensor pixel. In one aspect, each MOS sensor pixel in the array of sensor pixels is individually controlled and heated to predetermined temperatures.

As has been described, an array can include analyte-selective MOS sensor pixels, analyte-nonspecific MOS sensor pixels, or a combination thereof, including combinations of specific analyte-selective MOS sensor pixels that are selective for the same or different analytes. In the case of analyte-selective MOS sensor pixels, various potential mechanisms can be utilized to generate such selectivity in a sensor. It is noted that any mechanism, characteristic, or property that is capable of tuning a MOS sensor to increase the response selectivity to a given analyte or analytes is considered to be within the present scope. It is additionally noted that the selectivity of a single MOS sensor pixel can include an unambiguous determination of the presence of an analyte, as well as a statistically significant determination. Furthermore, selectivity can additionally be defined based on the intended use of the device. For example, a MOS sensor pixel can be categorized as selectively tuned to an analyte even though there may be cross-selectivity to another analyte that is unlikely to be present in the sample, or that is already known to be present in the sample. For example, a MOS sensor pixel that has cross-selectivity for an analyte of interest and nitrogen can be categorized as selective for that analyte when testing an air sample, provided the response to the analyte is detectable above the response to nitrogen.

Analyte selectivity can be achieved through a variety of mechanisms. In one aspect, the analyte selectivity is achieved by scanning through a range of temperatures at intervals using the MOS sensor pixels. Furthermore, a coating applied to the MOS active material can act as a filter to alter the selectivity of the sensor, such as, for example, a porous polymer coating. Additionally, in some embodiments, the filter need not be a coating on the MOS active material but can merely be coupled to or otherwise associated with the MOS active material in a fashion that allows the filter to perform its desired function and have a desired effect. For example, filtering can occur by altering the timing at which different analytes reach the MOS active material. There are multiple means for this purpose: 1. Filtering: porous material that is hydrophobic, that allows hydrophobic or nonpolar gas molecules to pass through. This material on the other hand can prevent water molecules (polar) from reaching the active material. 2. The porous material can absorb gas molecules under ambient temperature, a means of concentrating the gas molecules, at an elevated temperature, the gas molecules are desorbed and sensed by the active MOS material, resulting in selective and more sensitive detection. 3. Time delay or temporal resolution or different gases can be achieved by using a long pass structure that is made up of materials that can interact but not react with gas molecules. When a mixture of different gaseous molecules is passing through the pass structure, different types of gas molecules can be separated and subsequently detected selectively. In some examples, porous polymers can include without limitation, porous polymer networks with Tetrahedral monomers such as Tetrakis (4-Ethynylphenyl) Methane (TEPM), Tetrakis (4 Ethynylphenyl) Adamantane (TEPA) and Tetrakis (4-Bromophenyl) Adamantane TBPA. Polytetrafluorethylene (PTFE) can also be used in some embodiments. Additional examples include nanofiber-based filtering media, such as a collection of fibers having diameters about 10 nm to about 1000 nm. Nearly any other membrane, resin, or filter structure or material can be used as long as it does not impede the intended function of the sensor device. In a further embodiment, one or more catalysts associated with or within the MOS active material can be used to alter analyte selectivity.

In addition to changes to the active material itself, MOS sensor pixels can also be tuned to be selective to an analyte by adjusting the degree of heating applied to the active material. This differential heating (i.e., multiplexed heating) can be a characteristic designed into each MOS sensor pixel, or it can be a temperature regulation mechanism at the array level. All pixels in an array can be individually addressable electronically. A MOS sensor pixel tuned to heat the active material to an analyte-specific range can include any design element capable of achieving such tuning. Non-limiting examples can include alterations to the heating element material, limiting current to the heating element, alteration of the thickness of material layers between the heating element and the MOS active material, additional materials positioned between the heating element and the MOS active material, and the like, including combinations thereof.

MOS active materials in general can include any metal oxide material that is capable of being used in a sensor to detect an analyte. Non-limiting examples of such materials can include $SnO_2$, $V_2O_5$, $WO_3$, $Cr_{2-x}Ti_xO_3$, ZnO, $TeO_2$, $TiO_2$, CuO, $CeO_2$, $Al_2O_3$, $ZrO_2$, $V_2O_3$, $Fe_2O_3$, $Mo_2O_3$, $Nd_2O_3$, $La_2O_3$, $Nb_2O_5$, $Ta_2O_5$, $In_2O_3$, $GeO_2$, ITO, and the like, including combinations thereof and various stoichiometric ratios thereof. Thickness of the MOS active material can vary depending on the MOS sensor design and according to the tuning of the sensor, as has been described. Generally, the thickness of the MOS active material should be within the depth of change of the MOS work function but could also be thicker.

Additionally, the MOS active material can be doped, either to affect analyte selectivity or for other functionality of the sensor. Any dopant that is useful in the construction or use of the MOS sensor can be used to dope the active material. Non-limiting examples can include Pt, Pd, W, Au, In, Ru, B, and the like, including combinations thereof. In some cases, a dopant can include any useful catalyst. In other cases, a dopant can include a noble metal. It is noted that, in addition to increasing selectivity, the MOS active material can be doped to decrease selectivity towards an analyte or analytes. In this invention, the MOS active material can be doped MOS or undoped MOS.

The heating element of a MOS sensor can include any type of heat-generating component or structure capable of selectively providing heat to the MOS active material. In one aspect the heating element can be a resistive heating element that includes any type of conductive wire or other structure that can be locally heated by applying a voltage. The heating element can thereby heat the MOS active material to a desired temperature at which analyte detection is performed. Depending on the MOS material used, and the analytes being detected, a non-limiting operating temperature range can typically be from about 20° C. to about 600° C. The thickness, material, and/or structural configuration of the heating element can vary, depending on the design of the sensor and the desired analyte selectivity to be achieved. In some aspects, the heat element material can include a dopant to affect the heating properties of the material.

The temperature sensor can include any material or structural configuration that allows sensing and/or monitoring of temperature. In one specific aspect, for example, the temperature sensor can be a conductive wire that changes in resistance with a change in temperature, to thereby allow for accurate temperature monitoring. In some aspects, the heating element and the temperature sensor can be isolated from the MOS active area by an insulating layer. The thickness of the insulating layer can be varied to further affect the heating of the MOS active material.

Additionally, in some cases a feedback element can be coupled to the heating element and the temperature sensor to regulate heating by the heating element. The feedback element can be an electronic component or circuit that can regulate the temperature of the heating element to a set point or range of set points. Currently, temperature is checked by measuring resistive changes of the heating element that is Platinum (Pt), in other words, it is a heater as well as a thermistor. Platinum is very stable and its resistance changes as temperature increases. Thus, it can be used as a heater and a thermistor, and the two functions can be combined in the single element or device. Different temperatures can be achieved by applying different voltages or the same voltage at different duty cycles to the heater. Its temperature can be monitored by checking its resistance. All these can be achieved through an electronic circuit board.

The electrode materials can include any material capable of detecting a resistance change or other reaction at the MOS active material and transmitting a signal indicating that resistance change from the MOS sensor pixel. The electrode can be directly or indirectly connected to the MOS active material and can include the same or different materials for the detecting and transmitting of the signal. In one non-limiting example, the electrode can be in an interdigitated arrangement, the same or similar to that shown in FIGS. 1 and 2.

The sensitivity of sensor pixel arrays according to aspects of the present disclosure can be affected by a variety of factors. In addition to temperature sensors, MOS sensor pixel arrays can include various sensors to monitor and/or account for such factors. Non-limiting examples of such factors can include sensor effects due to temperature, humidity, aging, non-specific adsorption, flow rate variation, thermo-mechanical degradation, poisoning, and the like, each of which can lead to erroneous detections of analytes. Sensors that monitor one or more of these factors can be used to provide calibration to the array, to indicate needed service of the device, to indicate an inappropriate environment for analyte testing, and the like. Such sensors can be integrated at the MOS sensor level or at the array level, depending on the design of the device. Furthermore, such sensors can be external components integrated at the level of a printed circuit board (PCB) or other system level.

Additionally, one or more environmental sensors can be incorporated into the MOS sensor array or into the MOS sensor device interfaced with the array. An environmental sensor can thus detect at least one environmental condition. While any useful environmental condition is contemplated, in one aspect the environmental sensor can be a humidity sensor. Humidity can affect the sensor reading of the array, and as such, a humidity sensor can be utilized to calibrate the array to a given humidity level. As such, readings in an environment having a level of humidity that can affect the analyte detection and/or analyte concentration can be adjusted to compensate, thus providing much more accurate analyte analysis as compared to non-adjusted readings. Environmental sensors can be integrated at the MOS sensor level or at the array level, depending on the design of the device, or external to the array.

Figure 4:
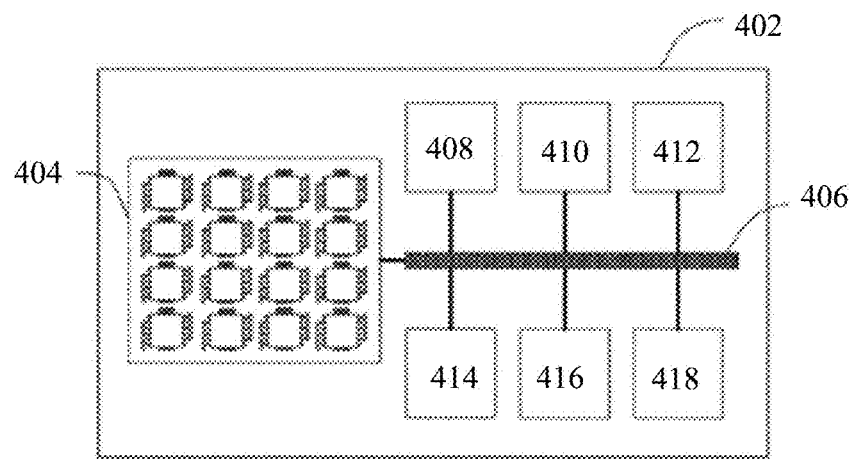
FIG. 4 is a schematic view of an analyte detection system or a sensor unit in accordance with an invention embodiment.

An analyte detection system operable to detect a plurality of analytes is shown in FIG. 4. Such a system can include an application specific integrated circuit (ASIC) 402, a MOS sensor array 404 functionally coupled to the ASIC 402, and an I/O module 406 functionally coupled to the ASIC and the sensor array, which can function to at least provide control and data communication there between. In one aspect, the ASIC and the MOS sensor pixel array can be monolithically integrated. In another aspect, the ASIC and the MOS sensor pixel array can be formed separately and coupled together. The I/O module can be any communication network, communications component, pathway, or connection including, without limitation, an I/O bus or other circuitry. The system may be composed of components that are separate from one another or may be a device where all the components are housed in the same enclosure or housing.

A given analyte detection system can additionally include a heating control module 408, that can be functionally coupled to the I/O module 406 and can operate to control heating of the plurality of heating elements in the MOS sensor pixel array 404. The heating control module may be referred to as a temperature controller and may be capable of controlling heating elements to heat different MOS sensor pixels to different temperatures simultaneously within the same array. Additionally, the heating control module can functionally couple with the temperature sensors and can thus monitor and/or control the output of the heating elements based on the temperature sensor readings.

Additionally, various modules can be included to address and readout signals from the array. For example, a readout module 410 can be functionally coupled to the I/O module 406 and can operate to read out data from the plurality of MOS sensor pixels in the MOS sensor pixel array 404. In one aspect, the readout module 410 is a display to display the identity and concentration of the analyte. An address module 412 can be functionally coupled to the I/O module 406 and can operate to address the MOS sensor array. The design of a given array, and thus the addressing and readout modules can vary in design and or functionality. For example, the ASIC 402 can be a CMOS ASIC, and therefore the addressing and readout modules can be based on CMOS processing. In other examples, readout can occur similar to a charged coupled device (CCD) readout, a PCB-level readout, or any number of other ASIC or non-ASIC readout and addressing schemes.

MOS sensor pixel array systems can also include various data processing and memory modules. For example, a system can include one or more data or signal processing modules 414 functionally coupled to the I/O module 406. Such processing modules may comprise a processor and can operate to accomplish a variety of tasks, including, without limitation, temperature scanning, comparison of spectrum like data with at least one peak, pattern recognition, pattern extrapolation, concentration or other quantitative analysis, qualitative analysis such as, for example, analyte detection and/or analyte mixture detection, environmental analysis, system status analysis, and the like. It is noted that various functionality can be incorporated into a dedicated module, such as, for example, an environmental analysis module. A data processing module can additionally perform signal processing functions on data received from the readout module, such as, for example, signal amplification and/or filtering. A given processing module function can be accomplished using common or dedicated circuitry and/or processors. For example, pattern recognition can be accomplished using a common circuitry with concentration analysis, or the two processes can have distinct circuitries. One or more nonvolatile memory modules 416 can additionally be included to store a variety of data, including a library, a standards database, calibration information that can be used to compensate for environmental factors, material aging, etc., pattern recognition data, and the like. Various algorithms useful for system control, data manipulation, and/or data analysis can also be resident in a memory module. Non-limiting examples can include matrix transform, genetic algorithms, component correction and principal component analysis, orthogonal signal correction-based methods, and the like.

The MOS sensor pixel array system can also include one or more control modules 418 functionally coupled to the I/O module 406. Control modules can operate to control system-level processes such as the heating module, the readout module, etc. Control modules can also operate to control functionality at the array or at the MOS sensor level, such as, for example, monitoring the temperature sensors and controlling the heating elements. In this case, the heating control module is included in the functionality of the control module. Additionally, the control module 418 can accept input and/or programming, thus allowing a user to interact with the system.

Accordingly, in one example signals are detected by the array of MOS sensor pixels and read out by the ASIC or other readout platform, the identities of the various analytes generating the signals are identified, and the concentration of each analyte is determined by the system with a high reliability during the life-time of the sensor array, irrespective of the environmental conditions and aging degradation. The present systems can further include a power supply (not shown).

The MOS devices and sensor arrays of the present disclosure can be fabricated according to any technique or method. For example, such arrays can be made using techniques such as micromachining, MEMS, and microelectronics techniques, printing technologies, chemical synthesis, and the like, including combinations of some or all of these techniques. Furthermore, in cases where an ASIC is used, the MOS sensor array can be integrated with the ASIC either monolithically by post-processing the array directly on the ASIC substrate or in hybrid fashion by fabricating the array separately and using wire-bonding or through-silicon vias (TSVs). In some cases, the ASIC can provide multiplex heating and sensing (MOS resistance change and local temperature), signal amplification, analog to digital conversion and digital output with address based data. It can also include programmable and memory blocks for signal processing, pattern recognition and calibration data for temperature and environmental effect compensations.

As to specific details, the microfabrication of MOS sensor arrays can be performed according to any number of well-known fabrication techniques, and one of ordinary skill in the art would readily be able to fabricate such an array once in possession of the present disclosure.

Figure 5:
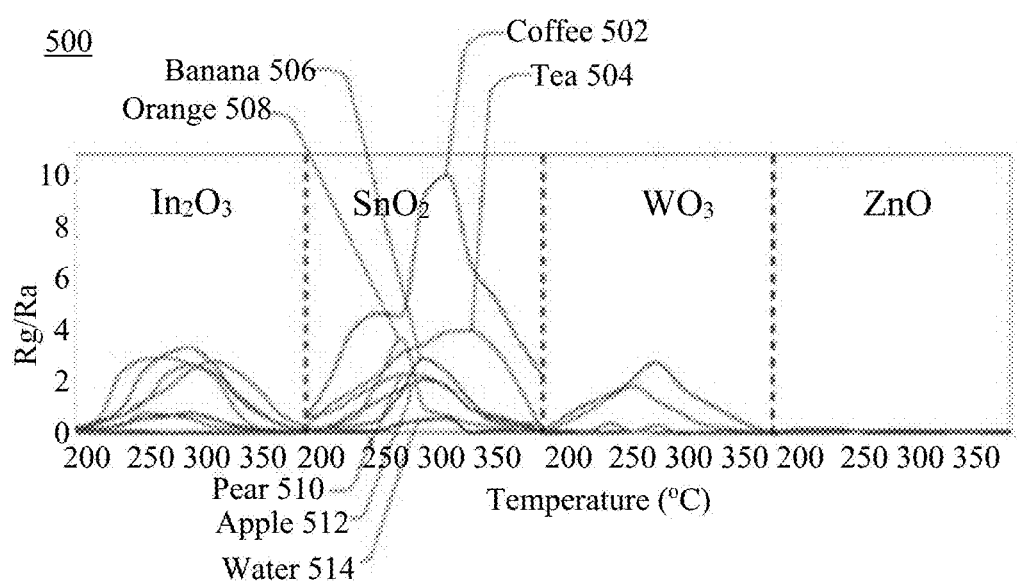
FIG. 5 is a depiction of a graph for determining a composition of analytes in a gas environment in accordance with an invention embodiment.

FIG. 5 depicts graph 500 of sample data of several different types of analytes exposed to different MOS active materials. Graph 500 depicts four different MOS active materials including $In_2O_3$, $SnO_2$, ZnO, and $WO_3$. Each of the four MOS active materials were incorporated into MOS sensors and were exposed to seven analytes. Each of the MOS active materials were then controlled to scan through a range of temperatures between 200-400° C. to generate response signals. The response signals were then assembled into the sample data displayed in graph 500. The x-axis of graph 500 represents temperature and the y-axis represents response intensity, that is the ratio of measurement reading (resistance of a sensing element in a pixel) over its baseline. The unit of a response signal is resistance (R) ratio. Note that the response intensity can be presented differently. As can be seen, the seven different analytes each reacted differently with the four different MOS active materials. For example, the reaction with the ZnO MOS active material was not dramatic and the resulting graph of the sample data for the seven different analytes are not very different from one another. Conversely, the reaction of the analytes with the $SnO_2$ MOS active material produced a graph of sample data where the different analytes are displayed quite differently from one another. Therefore, it may be inferred that $SnO_2$ is a better MOS active material for these analytes compared to ZnO. The graph of the sample data for the seven different analytes for the $SnO_2$ material is labeled identifying each of the analytes. For example, the sample data for the $SnO_2$ material includes coffee 502, tea 504, banana 506, orange 508, pear 510, apple 512, and water 514. Each of these sample data graphs displays spectrum-like behavior where the sample data for each analyte has at least one peak and/or an overall profile through the temperature range. The peak or profile is unique to each unique analyte. Therefore, a library of data or a standards database may be built to identify analytes. The standards database may be stored in a memory associated with the MOS sensor or may be located remotely, such as in the cloud, and accessed by components associated with an MOS sensor. In practice, an MOS sensor pixel may be exposed to an analyte, the MOS sensor pixel then scans through a sequence of predetermined temperatures to generate a response signal. The response signal is then assembled into sample data such as what is depicted in graph 500. The sample data is then compared with a standards database to determine an identity and concentration of the analyte.

In some embodiments, the peak or profile for each specific MOS active agent can be considered in combination with the peak or profile generated by one or more other MOS active agents over the same or different temperature ranges. Such a combination can generate an overall signature or profile that can be compared to the same combination in the standards database. In some embodiments, such processing can provide greater accuracy, sensitivity, or sophistication of analysis.

Figure 6:
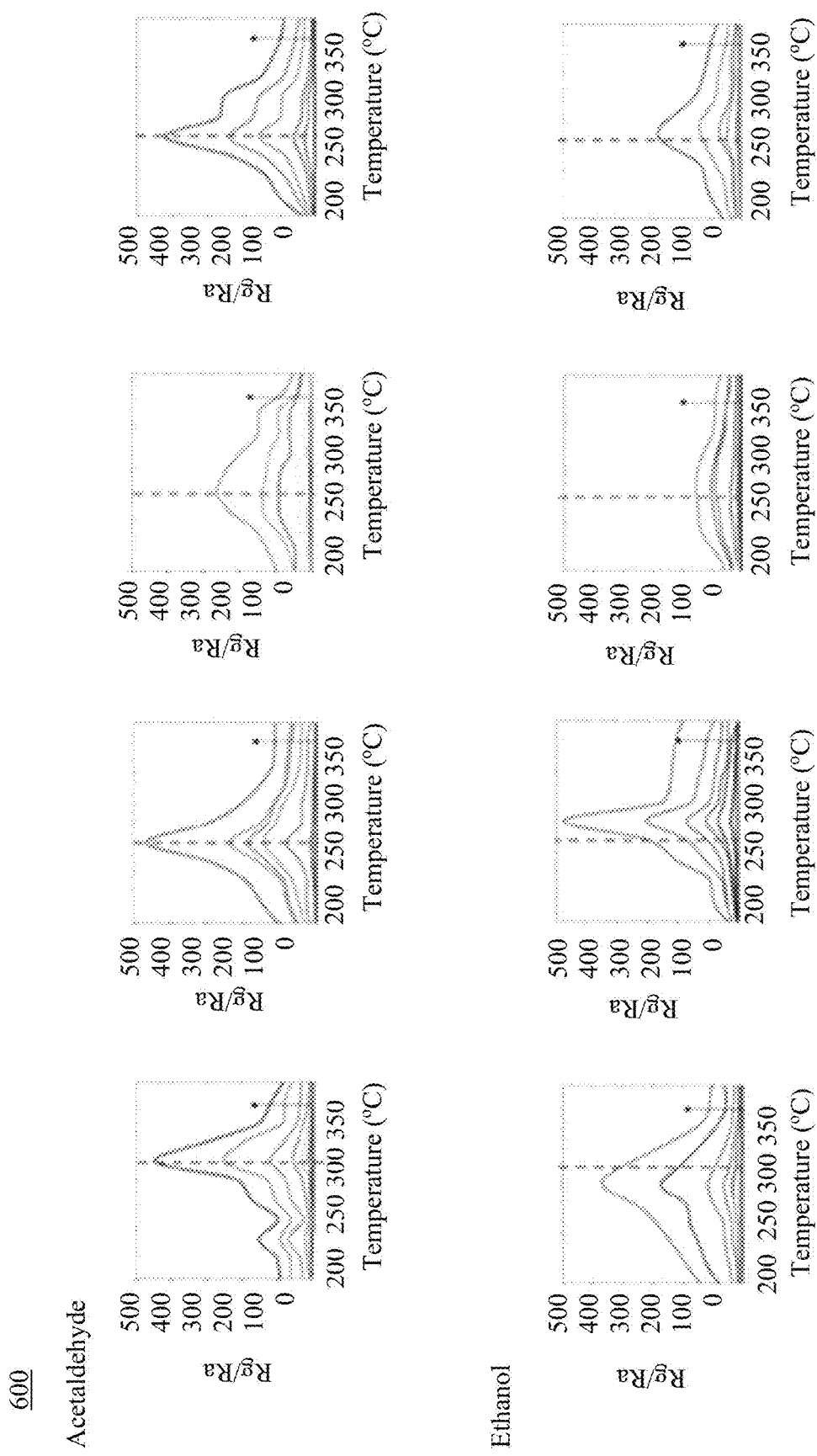
FIG. 6 is a depiction of a graph for building a library used to identify a composition of analytes in a gas environment in accordance with an invention embodiment.

FIG. 6 depicts graph 600 of sample data for two known VOCs exposed to different MOS active materials with different concentrations. Graph 600 depict sample data that is collected for known VOCs that is then used to build a library of data or a standards database that is then used to later identify corresponding analytes in a known or unknown sample, using MOS sensors, sensor pixels, and methods described herein. The top four graphs of graph 600 depict sample data for the VOC acetaldehyde collected using four different MOS active materials while the bottom four graphs depict sample data for the VOC ethanol. The four MOS active materials used for testing the acetaldehyde and the ethanol were $In_2O_3$, $SnO_2$, ZnO, and $WO_3$. Each of these four MOS active materials were incorporated into MOS sensors and then exposed to different concentrations of the acetaldehyde and then ethanol. For example, the top left graph shows six spectrum-like measurements of sample data. Each of the six spectrum-like measurements represents a different concentration of the acetaldehyde exposed to the $In_2O_3$ MOS active material. Because these data are used to build the library, the identity of the VOC is known and each of the concentrations was known ahead of the experiment. The sensor pixels with the MOS active materials were each exposed to several different concentrations of the same known VOC. For each exposure, the sensors were made to scan through the range of temperatures 200-400° C. at 5° C. intervals for 2 seconds each. The measured response signals were then assembled into the sample data displayed in the graph 600. The unit of a response signal is resistance (R) ratio. In each of the eight graphs the depicted arrow in the lower right corner indicates concentration increases and the measurement thereof. These concentration measurements are also added to the standards database to determine the concentrations of an unknown analyte while testing an unknown sample. As can be seen, the sample data in each of the eight graphs displays spectrum-like behavior where the sample data for each VOC has at least one peak and/or an overall profile. The peak/profile is unique to each unique VOC for each active MOS material over each temperature range.

For a given pair of metal oxide and gas or VOC, the response is also temperature specific. The library or database can be built according to the peaks featured in graph 500 and molecular structures of a set of gases or VOCs given the metal oxide used. Moreover, in the case of multiple gases or VOCs, math models currently used in signal processing and optical spectroscopy, can be used to de-convolute the data of measured sample, and gas or VOC species identities, as well as their respective concentrations, can be determined according to the database. Such deconvolution would be used to reverse the effects of convolution of the recorded data f from the multiple gases or VOCs. In general, this may be achieved by finding a solution of a convolution equation such as Equation 1:

$$(f \times g) + e = h$$

where e is a noise emanating from the recorded signals. The deconvolution is usually performed by computing the Fourier transform of the recorded signals h and the transfer function g.

Figure 7:
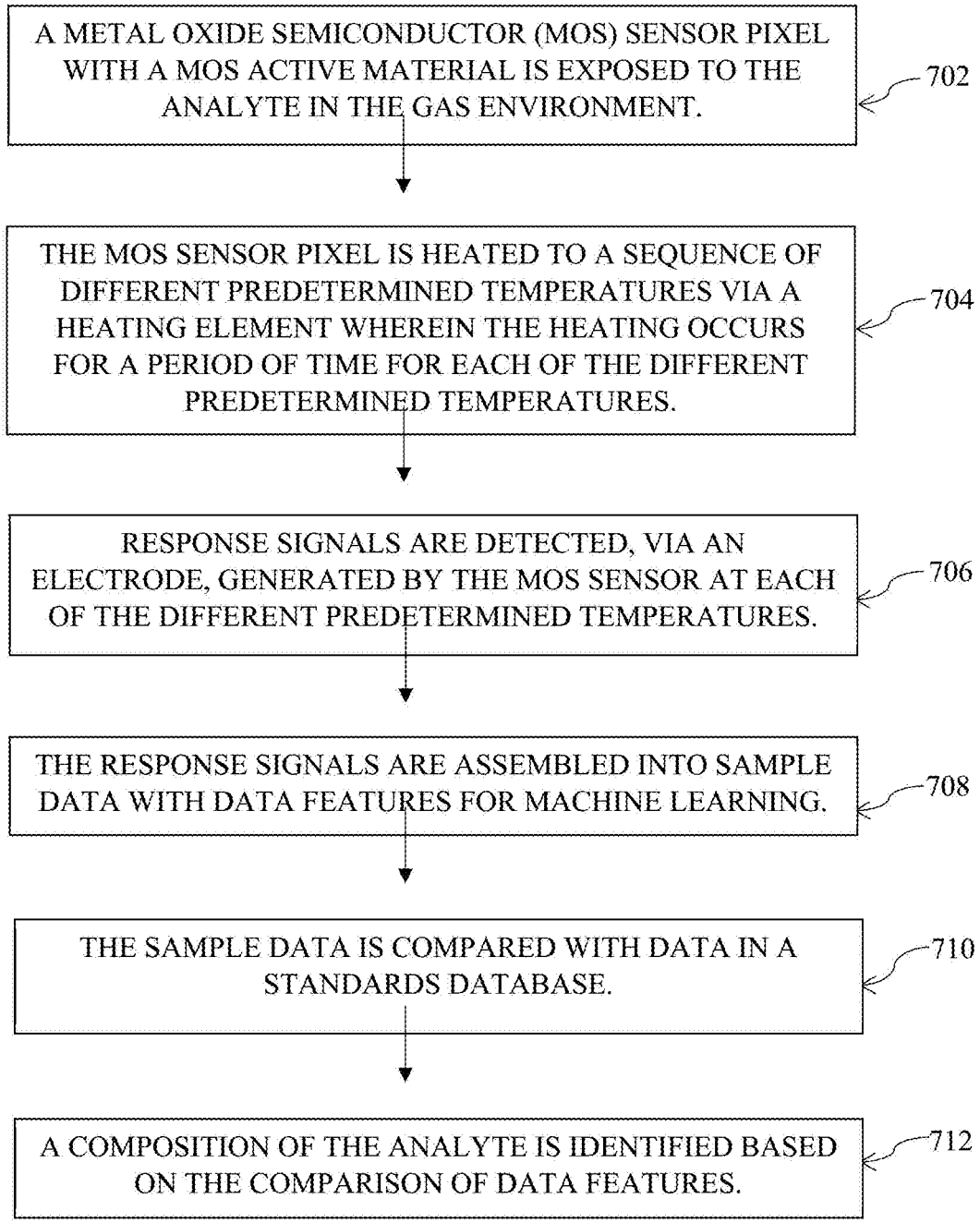
FIG. 7 is a depiction of a method for identifying an analyte in a gas environment in accordance with an invention embodiment.

As is shown in FIG. 7, the present disclosure additionally provides exemplary method 700 for identifying an analyte in a gas environment. Such a method can include exposing a Metal Oxide Semiconductor (MOS) sensor pixel with a MOS active material to the analyte in the gas environment, as in block 702. The method further includes heating the MOS sensor pixel to a sequence of different predetermined temperatures via a heating element wherein the heating occurs for a period of time for each of the different predetermined temperatures, as in block 704. The method further includes, detecting response signals via an electrode, generated by the MOS sensor pixel at each of the different predetermined temperatures, as in block 706. The method further includes, assembling the response signals into sample data with data features for machine learning, as in block 708. The method further includes comparing the sample data with data in a standards database, as in block 710. The method further includes identifying a composition of the analyte based on the data features, as in block 712.

With the above generated smell data, the question is how to create smell information from the raw data, how to create an organized and structured database and what pieces of data and in what format have to be included to create useful smell information.

MOS sensors, for that matter any sensors, by themselves directly create data and the information has to be created by human intervention i.e., by structuring and organizing the data in a defined manner with a purpose and bringing in other associated information and relating them with the raw data. For creating comprehensive and meaningful smell information, it is critical to consider two things. First, the structure in which the smell data needs to be organized for a database and second, how the database has to include all the necessary associated data, i.e., smell condition data, instantly for example, geographical location, time, source of smell, preferably at the same instant data is collected to create a more comprehensive smell information. The true key element is how all the data and different data types that are included to form a database associated with a particular gas create a useful piece of information.

A data type is the most basic and the most common classification of data. It is this through which the compiler gets to know the form or the type of information that will be used throughout the code. A data type is an attribute of data which tells the compiler (or interpreter) how the programmer intends to use the data. So, data type is a type of information transmitted between the programmer and the compiler where the programmer informs the compiler about what type of data is to be stored and also tells how much space it requires in the memory.

A data type is a set of representable values. Every representable value belongs to at least one data type, and some belong to several data types. SQL supports three sorts of data types: predefined data types, constructed types, and user-defined types. Predefined data types are sometimes called the "built-in data types", though not in this International Standard. Every predefined data type is a subtype of itself and of no other data types. It follows that every predefined data type is a supertype of itself and of no other data types. User-defined data types can be defined by a standard, by an implementation, or by an application. A constructed type is specified using one of SQL's data type constructors, ARRAY, REF, and ROW. The type is either an array type, a reference type, or a row type, according to whether it is specified with ARRAY, REF, or ROW, respectively. Array types are the only examples of constructed types known generically as collection types.

Collecting a particular smell data from MOS gas sensors by temperature sweeping and treating the raw data with the smell condition i.e., the environment associated with a particular smell data to create a more comprehensive smell information, is unique to this invention. The primary concepts of the invention are, how the raw data or core smell data is treated and organized, and second how other or associated data is included with the core data to create a structured database for meaningful smell information generation. The smell information created in the above manner has more value. To enable this invention, it is not only about the core smell data, but its organization and coupling with the smell condition data such as humidity, geographic location, outside (geographic location) temperature etc. The core smell data will be fused with other associated smell condition data and then stored in a database to create a smell information template. This smell information template is a standard for AI or machine learning or any mathematical technique to be implemented.

Once the raw smell data from MOS sensors is available, then the next step is to structure the core smell data followed by normalizing the smell data. The smell data comprising of temperature sweep data from each of the metal oxide pixels of the sensor array forms the core piece of smell information. Subsequently, including the associated conditions of smell to the core smell data forms a structured database. Once such a structured database is created and stored either in a local computer or in the cloud, there are many applications one can develop for using the information from the structured database. Subsequently, Artificial Intelligence (AI), Machine Vision (MV) or any other mathematical techniques can be applied for analyzing the information from such structured databases. Smell information according to an embodiment is illustrated in the accompanying drawings and detailed in the following description.

Figure 8:
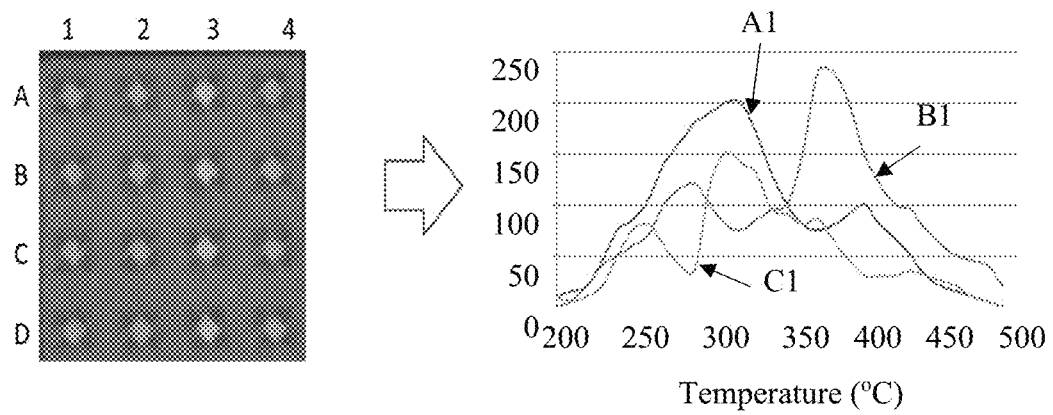
FIG. 8 is an example of collecting smell information using multi-dimensional sensing in accordance with an invention embodiment.

FIG. 8 is an illustration according to an embodiment of the invention showing a visual representation of the data created from individual sensor pixels of an MOS sensor array by temperature sweeping. On the left is the image of the MOS sensor with individual pixels arranged in a first vector A to D and a second vector 1 to 4. On the right, three different graphs depict the responses of individual pixels for a single chemical, for example acetone, which is considered at the highest concentration and is depicted in different shades (or colors). Three graphs correspond to three different sensor pixels, for example A1 to the first pixel in row A and column 1, B1 to the first pixel in row B and column 1, C1 to the first pixel in row C and column 1. Only three pixels' response is shown for clarity.

Figure 9:
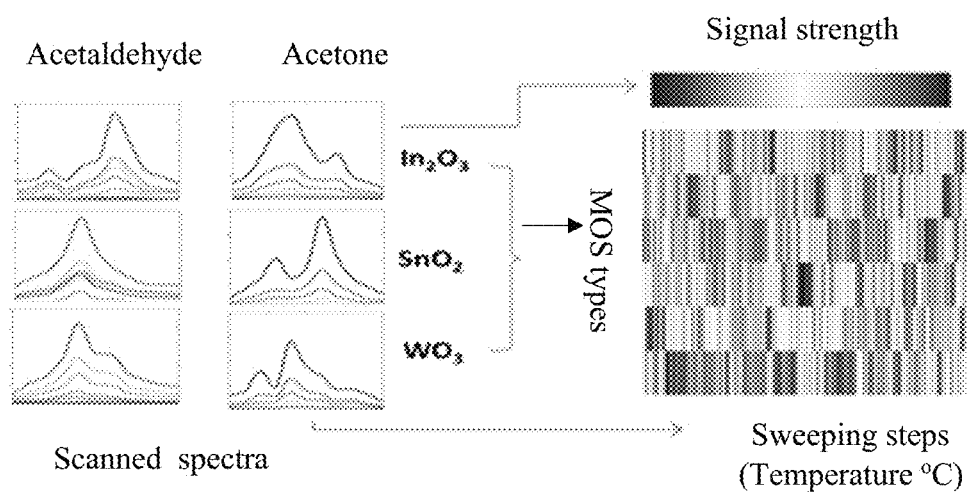
FIG. 9 is an example of transforming smell information to digital data in standardized format in accordance with an invention embodiment.

FIG. 9 is an illustration according to an embodiment of the invention of visual representation of the core smell data created from sensor pixels of a sensor array by temperature sweeping into a heat map or core smell information. It illustrates how the database visually looks in a two-dimensional space. The left graph of FIG. 9 shows the actual smell data collected for two different chemicals, for example Acetaldehyde and Acetone, by temperature sweeping. Different shades (or colors) in the graph depict different concentrations of chemicals which are used for the data collection. Three different types of metal oxides response, $In_2O_3$, $SnO_2$, $WO_3$ are shown. The heights or peaks in the graphs represent the signal strength. On the right, the vertical axis (y-axis or a first vector) represents metal oxide type and the horizontal axis (x-axis or a second vector) is the temperature at each sweeping step. Typically, the temperature range will be 100° C. to 500° C. with a sweep step of 1° C. Once the data is collected for a chemical as shown on the left-hand side, the right-hand side map is created for that particular chemical after the normalization of the data. The map generated is similar to a heat map. Each color (or shade) represents a different signal strength. The core smell information comprises three-dimensional data represented in a two-dimensional space or as a two-dimensional array. First dimension is a different type of metal oxide, the second dimension is temperature at sweep steps and the third dimension is the signal strength data from the metal oxide at a particular temperature after normalizing the data. Visually this is a three-dimensional information represented onto two-dimensional space as a heat map or as a two-dimensional array.

Figure 10:
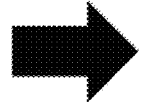
FIG. 10 is a data normalization method in accordance with an invention embodiment.

A structured information template according to an embodiment is shown in FIG. 10. The template comprises a sensor pixel material code which corresponds to pixel's metal oxide material in the MOS sensor, response data corresponding to each of the sensor pixels through the temperatures at sweeping steps. The data is recorded in a particular format with a first vector corresponding to the sensor pixel material and a second vector corresponding to the temperature at sweeping steps. This data forms the core smell data. In addition to the above data, humidity, location position or geographic location (longitude, latitude, and altitude), location (ambient) temperature is also recorded along with the core smell data. All the above data will be recorded at the same instant when the smell data is collected and structured as a smell information in a smell information table or smell information database. Besides the above data, there are provisions for recording any other relevant data such as time of collecting the smell data that can be incorporated and formed into a smell information. If the source of the smell is known, it is possible to manually input a source. Many natural things have their unique shapes, color, and smells, for example, flowers, fruits, plant leaves, animals. This is also true for man-made products, such as red wines, cigarettes, perfumes, etc. When a sensor is taking smell information from an object, a camera can also take its image at the same time. The name of the source can be input in two ways: identifying the object by image information from a database or manually inputting the source information if it is known. An image or a photo information of the source can also help identify the object where the smell is generated, hence the image can also be taken when small data is being taken. If the source of the smell is not known, the sensor can record the data and generate the structured smell information directly with source information as blank. This structured smell information generation with the associated data is a key part of the information. This structured database is indexed to identify or as an identification of a smell record and facilitates quick retrieval of a smell information. The library of smell information or a smell standards database can be built to identify analytes by recording the data of known smells along with their associated information. This can be either stored locally on a computer or centrally on a cloud and can form a centralized structured database of smell information. The raw data collected in the above template is then normalized as shown in FIG. 10. The table or template comprises a first vector and a second vector representing metal oxide sensor pixels and temperatures at sweep steps, respectively. The top table is the raw data, and the bottom table is after normalization. Typically, standard value is used to normalize. The highest value in a row of data is used to divide every data point in that row to generate a ratio. Ratios will have decimals and it is not very easy for the computer to handle the decimal. Hence, the ratios are multiplied by a number, for example one thousand, to create a range between 0 and that number (ex. 1000) to make a 3-digit value as a standard. Once the data is normalized it is brought within a particular range as can be observed from the bottom table. The goal of normalization is to change the values of numeric data in the dataset to a common scale, without distorting differences in the ranges of values. When features have different ranges, then normalization is required for the machine learning algorithms to work efficiently. Normalizing the data from metal oxide sensors in this particular utility is novel, because it makes the comparison of smells easy for various smell related applications. For example, the hospital rooms are cleaned every day. Sometimes they use a lot of very high concentrations of cleaning agents, sometimes very low or sometimes skipping the cleaning that will generate very low values of smell data. Every day or every couple of other days the same chemical may be present in the same location, but the value changed. Now to analyze information in such situations, normalization is the only way. Once the data is normalized, it is easy to identify if the room has been cleaned or how many days it has been cleaned or how long it has not been cleaned. It is easier for the system to identify what the sensors have been exposed to. Normalized data is good for identifying the gas species. However, it loses the feature and absolute concentration. Therefore, one strategy is to use normalized data for identification, and use unnormalized data for quantification.

Once the data is normalized, an information table called structured data is created. The structured data has an advantage that whenever a piece of information is queried or accessed, it has a fixed format. With structured data, the goal is to create a fixed format of data. When the data is created from many input sensor sources in the same format, implementation of AI will be easy. All the known AI technologies can be applied because of the structured data. Once a structured information or structured database is generated, the next part is how to analyze or utilize that information. Creating such a structured database is the key part for the invention. There is no industry standard for data structure and the uniqueness is to create such standard format or database or table for use in smell applications.

Figure 11A:
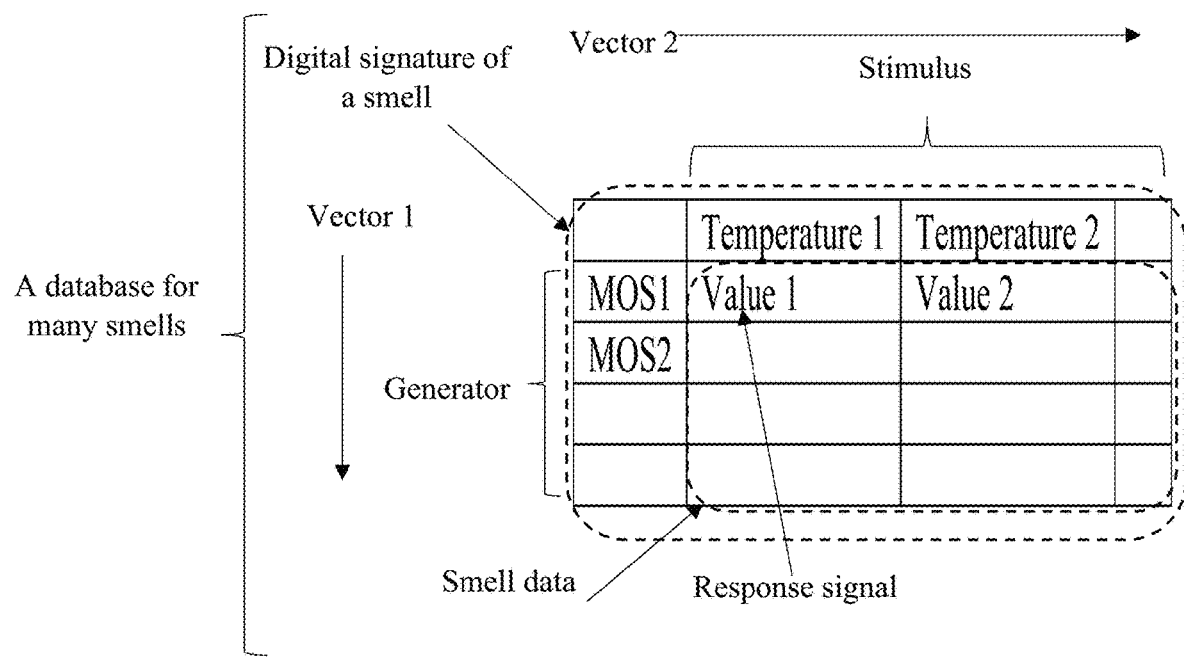
FIG. 11a is an illustration of a database comprising many smells depicting the terminology involved in a smell database.
Figure 11B:
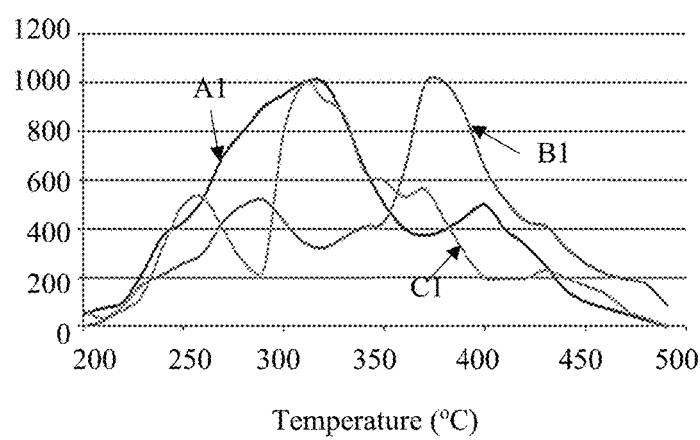
FIG. 11b is a depiction of normalized data and heat map visualization in accordance with an invention embodiment.

FIG. 11a is an illustration of a database comprising many smells depicting the terminology involved in a smell database. As depicted in FIG. 11a, a response signal is a measurable response of the sensing element or MOS pixel in a sensor, including changes in electrical properties (resistance/impedance). It is an analog signal, convertible and recordable in digital forms. A generator is a sensor, or a sensor pixel of a sensor array or MOS active material exposed to an analyte in a gas environment and is capable of generating a response signal. A predetermined stimulus is an input stimulus provided to a sensor in order to measure its response that corresponds to the predetermined stimulus, herein it is a sequence of predetermined temperatures. A smell data is an array comprising response signals of a plurality of MOS sensor pixels at a plurality of predetermined temperatures wherein the plurality of MOS sensor pixels is a vector, and the plurality of predetermined temperatures is another vector, wherein the vector is defined as a one-dimensional array used for storing values. A digital signature of smell comprises differing responses across the MOS sensor pixels at a plurality of predetermined temperatures in an array which can be used as a type of "fingerprint" or digital fingerprint or digital signature or pattern to selectively distinguish between analytes that are indistinguishable or difficult to distinguish by the response characteristics of individual MOS sensor pixels alone. A smell database comprises digital signature of plurality of smells and is a relational database. Various database operations which vehicles through which users and applications have access to data in a relational database can be performed on the smell database. FIG. 11b is an illustration of a heat map generated using the normalized data according to an embodiment of the invention. The digital signature of a smell both graphically as well as in an array form for three different MOS sensor pixels i.e., A1, B1, C1 are shown in FIG. 11b. Generation of heatmap typically comprises steps to convert the normalized values in the bottom table of FIG. 10 to the graphic or heat map. The highest values are depicted in red (or darker shades) and the lowest values in blue (lighter shades) and the range between the high and low with different mapped colors (or shades) according to an embodiment. A heat map or heatmap is a data visualization technique that shows magnitude of a phenomenon as color in two dimensions, depicting values for a main variable of interest across two axis variables as a grid of colored squares. The axis variables are divided into ranges like a bar chart or histogram, and each cell's color indicates the value of the main variable in the corresponding cell range. The variation in color may be by hue or intensity, giving obvious visual cues about how the phenomenon is clustered or varies over space. There are multiple ways to create the graphic or maps from values. This particular format is advantageous as standard tools are available to analyze the information provided in this particular heat map format. The two techniques numbers or values of the data or maps based on the color intensity are equally acceptable for further analysis. There are many AI tools or data analysis tools which can take the above data or map as an input for further analysis. The heat map can act like a photograph and any image analysis tools or image recognition tools can be easily implemented in analyzing the information. In summary, either the numeric data points alone for data analysis, or heat map or image created from the numeric data are acceptable formats, but heat map is a preferable format according to an embodiment of the current invention.

Figure 12:
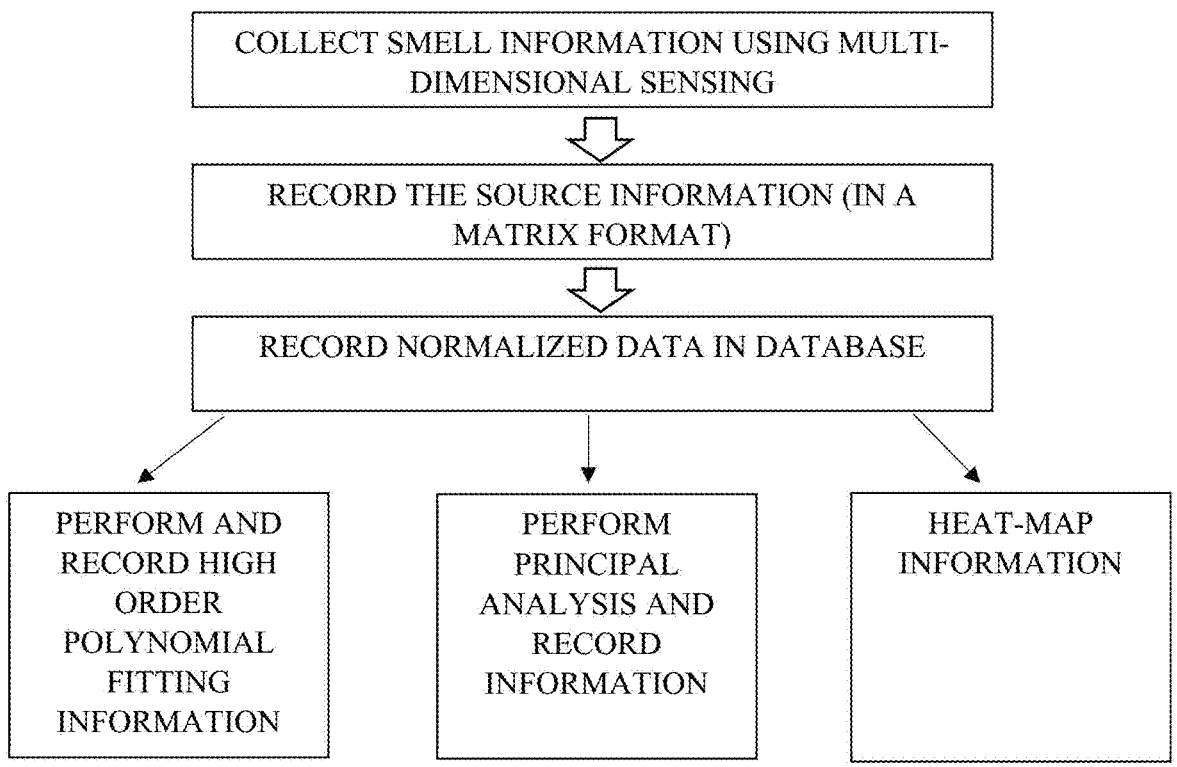
FIG. 12 is a flowchart for building a normalized database in accordance with an invention embodiment.

FIG. 12 is an illustration of a flowchart for building a normalized database according to an embodiment of the invention. It comprises collecting the smell data using multi-dimensional sensing, recording the source information in the computer-readable matrix format (as shown in FIG. 10), normalizing the data and recording the normalized data into the database. From this normalized data one can do multiple options like performing and recording a high order polynomial fitting information, performing a principal analysis and/or recording the information and/or generating a heat map information. Each of these techniques has its unique advantages based on the use case or scenario of analysis.

With the advent of computers and computer technology, images and sounds have been digitized. They are now part of our lives. The idea is to digitize smells or odors. This will have an impact on many systems including olfactory science and the flavor and fragrance industry. Currently, there is no standardized way of specifying an odor. Digitization will allow us to precisely specify an odor, which will allow us to electronically store and transmit fragrances or smells or odors. One major goal is to encode odors towards digitization of the smell.

Figure 13:
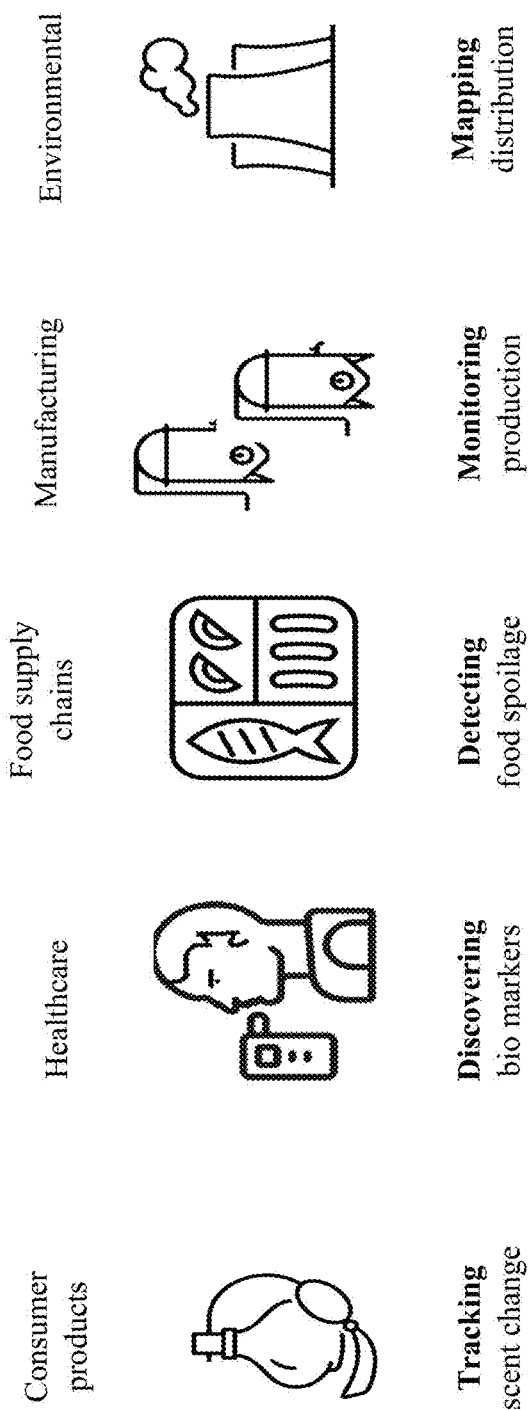
FIG. 13 is an example of potential applications of digital smell in accordance with an invention embodiment.

FIG. 13 is an illustration of application scenarios or use cases for the smell information according to an embodiment of the invention.

Figure 14:
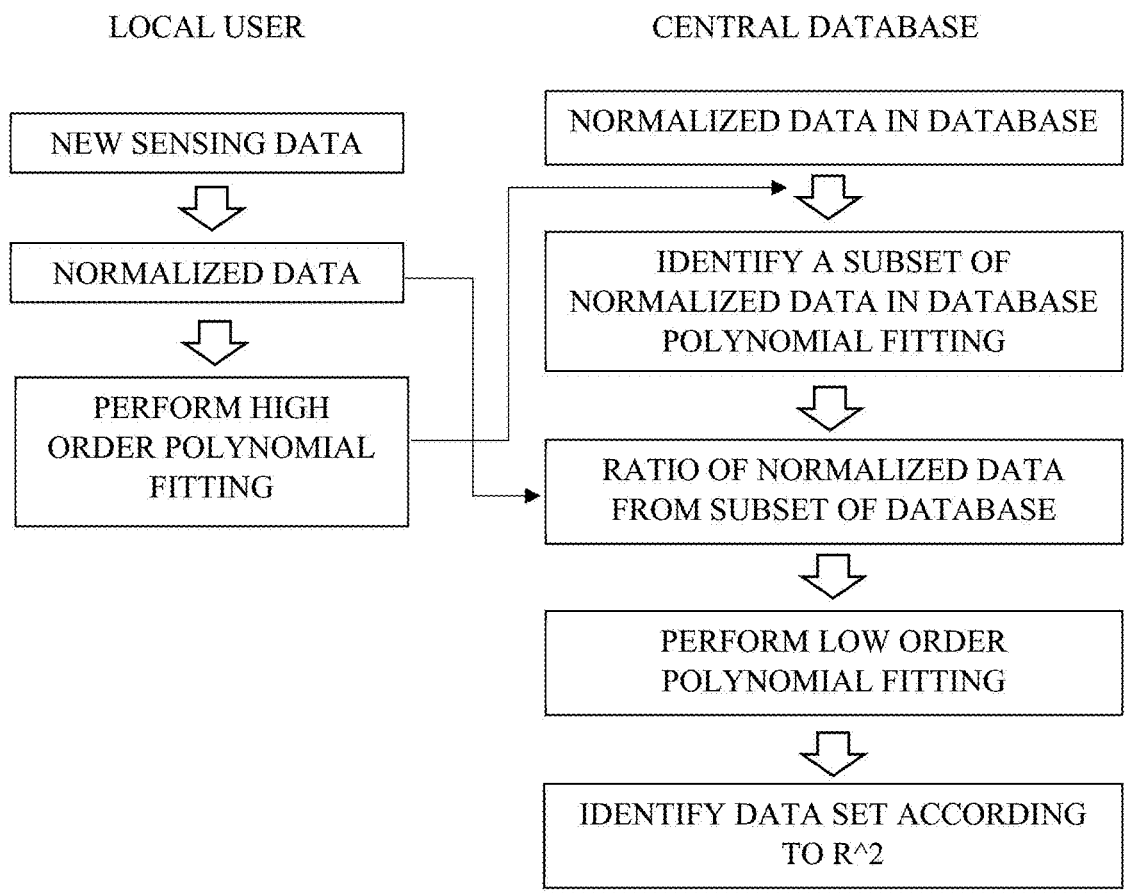
FIG. 14 is a flowchart for identifying matched data sets in accordance with an invention embodiment.

FIGS. 14 to 18 illustrate flowcharts for application use cases according to an embodiment of the invention. FIG. 14 Identification (identify unknown smell), FIG. 15 Monitoring (see what are changing over time in given location), FIG. 16 Tracking (see what happen overtime and locations), FIG. 17 Discovery (to find the unique features associated with given conditions), and FIG. 18 Mapping (location distribution) using structured database of smell information according to embodiments of the invention. Each flowchart is for a different use case scenario. The process to the left is on the user end, and on the right is the database. Each application case has a different flowchart and there is a different process to create the information and to use the information.

The library of data or a standards database that is built to identify analytes can be used to build a centralized structured database of smell information. FIG. 14 corresponds to the flowchart to identify a matched data set or simply identification of a sample smell input by the user. Towards the left side shows a new smell data from the user end, it is normalized and a higher order polynomial, usually greater than $2^{nd}$ order is fitted to obtain the new smell information. The central database comprising normalized data is then searched by identifying a subset of normalized data in database polynomial fitting and also by considering the ratio of normalized data of new smell with that of the normalized data from the subset of the database. Then a low order polynomial is fitted, and the best fit is identified using $R^2$ data. The R-squared is a statistical measure of how close the data are to the fitted regression line. It is also known as the coefficient of determination, or the coefficient of multiple determination for multiple regression. The smell information corresponding to the highest $R^2$ is the closest identified smell to the new smell that the user has provided. The identified smell information from the database is presented to the user.

Figure 15:
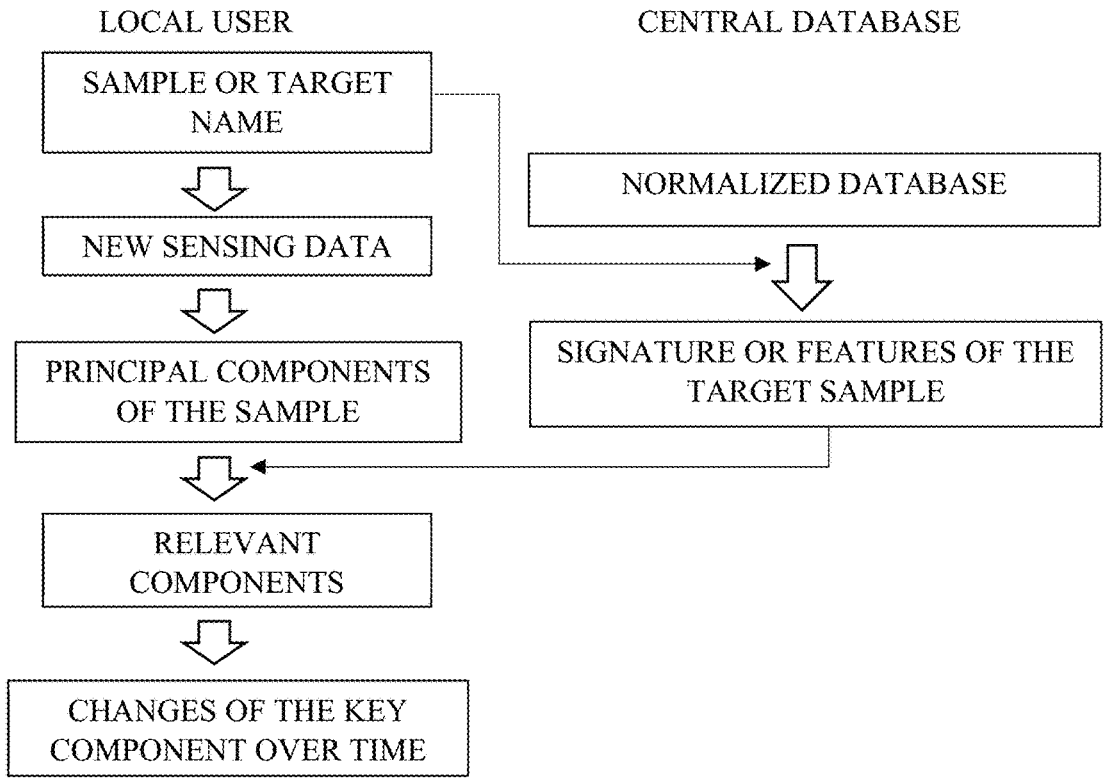
FIG. 15 is a flowchart for identifying the change of a particular target in accordance with an invention embodiment.

FIG. 15 corresponds to the flowchart for identifying the change of a particular target smell or tracking a target smell for its changes over time. Towards the left side shows a local user providing a sample smell data or a target smell name. This new sensing data is analyzed for its Principal Components in the smell and relevant components are extracted. The sample smell data or a target smell name is used to retrieve the signature or features corresponding to the target sample. These features are used as standard values to compare the changes of the key components over time.

Figure 16:
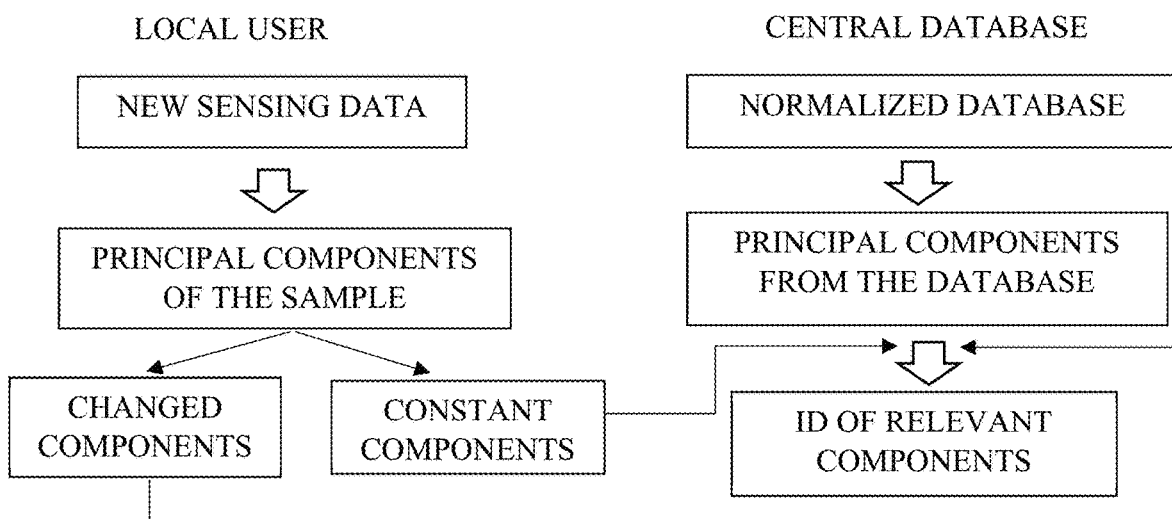
FIG. 16 is a flowchart for observing the changes of a set of unknown features in accordance with an invention embodiment.

FIG. 16 corresponds to the flowchart for observing the changes of a set of unknown features, i.e., for monitoring. Towards the left side shows a local user providing sample smell data or new sensing data. This new sensing data is analyzed for its Principal Components in the smell data and relevant constant and changed components are extracted. These changed and constant components of the sample smell data are used to retrieve the identification of the relevant components from the central database. The normalized database first performs the principal component analysis on the central database smell information and then retrieves the identification of the relevant components.

Figure 17:
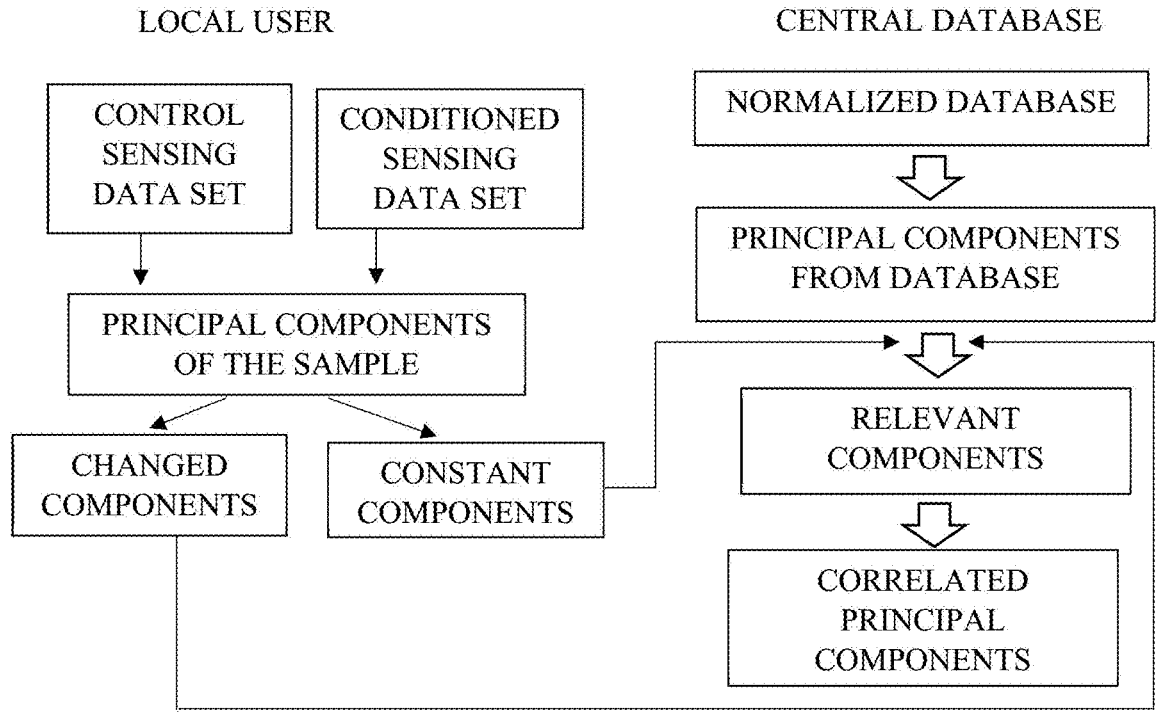
FIG. 17 is a flowchart for identifying common features over time or among a population in accordance with an invention embodiment.

FIG. 17 corresponds to the flowchart for identifying features over time or among a population i.e., for a discovery of smell. Towards the left side shows a local user providing sample smell data in terms of controlled sensing data set and conditioned sensing data set. This new sensing data is analyzed for its Principal Components in the sample smell data and relevant constant and changed components are extracted. These changed and constant components of the sample smell data are used to retrieve the identification of the relevant components from the central database. The normalized database first performs the principal component analysis on the central database smell information and then retrieves the identification of the relevant components. The correlation among the principal components from the sample smell and that of the central database retrieved smell information is provided to discover how the sample smell corresponds to the smells stored in the database.

Figure 18:
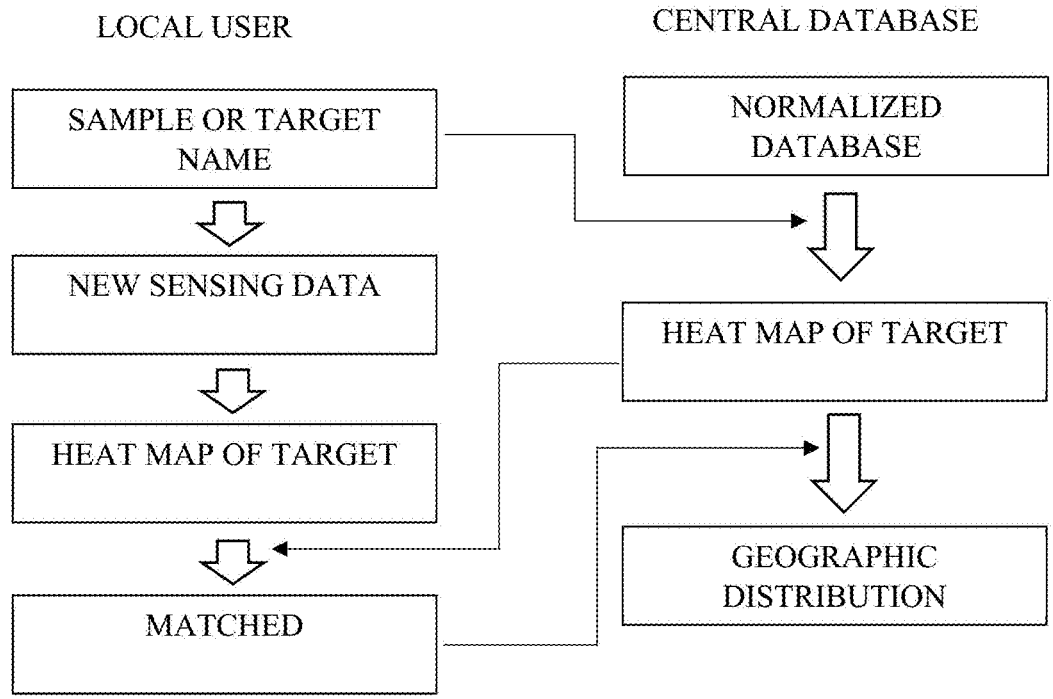
FIG. 18 is a flowchart for identifying the changes of targets geographically in accordance with an invention embodiment.

FIG. 18 corresponds to the flowchart for identifying the changes of targets geographically i.e., for mapping the smell. Towards the left side shows a local user providing a sample smell data or a target name. This new sensing data is used to generate a heat map of the sample smell. This new smell data or target name is searched in the central database which corresponds to a normalized database. The heat map of the standard of the target is retrieved from the central database. When there is a match in the heat map of the sample smell and the heat map of the target from the central database, geographic distribution of the smell information is provided to the user, i.e., the smell information is mapped geographically.

EXAMPLES

The following examples pertain to further embodiments.
There are many applications one can develop for using the information from the structured database available either in the cloud or in a local computer. One such application example is that of an alert system that can give an alarm or some alert message. As an example, in a multi storied building different rooms or different stories of building can be installed with sensor systems. When a subset of the sensors from the installed sensor system senses some incumbent smell then that analyzed information can be sent as a security alert to the building administration or building security department. The idea is that the sensor system linked to a structured database can provide alerts according to the information collected from some or all sensors. The alert system can be programmed by end-users according to their requirement using simple applications and/or using AI and mathematical techniques. Suppose in the same multi storied building, if there is only one or very few among all the sensors installed into the building to give some smell information, then the message would alert for some unusual activities that need attention. If the data indicates system wide smell information change, it may suggest an issue in the ventilation system. The idea here is that once the structured databases already exist either in a local computer or in the cloud, application layer development, as an executable program code on a computer, can be built upon the information layer as per the application's need. The above is a smell identification example, wherein the smell information from the existing structured database is compared with the smell data generated from the installed sensors towards an alert system application.

Another way to use the information from the structured database is for retrieving smell information provided the user can provide some smell related keywords. As an example, the user can query that "I need smell information associated with Alcohol" and then the system should provide relevant smell information of ethyl butanoate, butyraldehyde and isopropanol to the user. Suppose if all hospitals collect the smell data and all the smell data will go to the cloud or computers of government agencies or health organizations and they want to do research or a study on COVID-19, or see what happened in the hospital or the location near a patient? In such cases, the doctors can check in smell differences from various hospitals or check specific smells near a patient or they can request information among all the different facilities providing similar COVID care to understand the differences. Studies have reported a potential breath-borne volatile organic compound (VOC) biomarker for COVID-19. Higher levels of ethyl butanoate were detected in exhaled breath of COVID-19 patients than healthy controls/health care workers, lung cancer (LC) patients and backgrounds. The monitoring of ethyl butanoate, butyraldehyde and isopropanol could lend considerable support in rapidly screening COVID-19 and alerting the presence of COVID-19 patients in particular environments. (Breath-borne VOC Biomarkers for COVID-19, medRxiv, Cold Spring Harbor Laboratory Press, Chen, Haoxuan; Qi, Xiao; Ma, Jianxin; Zhang, Chunyang; Feng, Huasong; Yao, Maosheng; 2020, http://medrxiv.org/content/early/2020/06/24/202.06.21.20136523). Thus, a breath VOC database can be used for disease monitoring, disease diagnosis and biomarker discovery. The diseases may be cancers, infections, or genetic diseases that affect normal metabolisms or physiological conditions of the bodies.

The idea is to convert the smell data into smell information and to make it more valuable. Collecting more and more information and passing all the information to a database and then repeating this data collection and passing loop together is very useful and increases the value of the information in the database. As an example, consider Google® maps, which are used by the cars/vehicles and all the information on the location, the city highway traffic information is collected and all this information of the traffic along with the location is highly valuable. Similarly, the smell information. The sensors are used for generating the smell information along with the source-associated information which makes it more valuable.

Smell information which is a structured database will be saved in memory either in cloud or in local computers. Additional software can be developed to extract information and then provide to the end-user. Users can subscribe for the information and then depending on their case can use different software to extract the information out from that database. For example, for environmental purposes, software can be developed to extract information related to the environment, similarly for health-related cases, software can be developed to extract the information related to health. So, a different software can extract different sets of information.

There are two ways to use the information, one is through AI where the information can automatically extract and then give the user a notice or alert proactively and the other is the user can type in certain requests like a Google® search and the information will be the output along with analysis.

In an embodiment, the invention has two layers. The first layer has the raw information database. That is typically controlled and may not be available to the user. Second layer has the normalized information database. Depending on the business of the users, they can subscribe to the normalized information database and/or to the original raw information. Typical subscribers can be corporations, government agencies, individual users etc. For Example, a government body can subscribe to the information related to the environment, research organizations on public health can subscribe for health related smell information or a cell phone user can subscribe if the cell phone has an individual sensor either embedded in the cell phone or mobile device or in their home or in their computer. As an individual, one can subscribe to a part of the database or for certain applications. Another example of use in industry can be pharmaceutical or a factory which does fermentation or a factory that makes cheese, or vinyl, or for that matter any industry which works with chemicals or produces some smell data to understand or track different states of the process which are typically related to different or unique smells. Users subscribe to the information database, can collect information, upload the information, and compare the new information with the old existing information etc.

There are multiple ways to use the information, for example, tracking to know when something changed, identify to know what the presented smell is, and discover what is in the smell database.

One example is these sensors can be installed near the toilet in the restroom at one's home. Everyday smell data will be collected. If the health of the person living in the house has deteriorated, then the doctor or related person can go back to look at the database and see everything associated with smell to determine possible health related issues like cancer or an individual's food habits. During the smell data collection, certain smells are associated when an individual is in a healthy state and if suddenly the individual gets very sick and then the smell information of those days may be associated with that illness.

Another example is the discovery of reason (smell data feature) for an anomaly using the smell information. One can take a breath analysis every day and save the smell data to the database. But over time if one suddenly feels uncomfortable and comes to know that they are suffering from lung cancer or so, then one can go back to and analyze the database and then see how the data features associated changed over time and then identify what signals in the database are to be associated with lung cancer. And then from the signals and also through the database one can identify the smell information associated with lung cancer. That is to say that the signals associated with certain compounds, chemical compounds and then based on the chemical compounds, one can discover those signals as biomarkers for cancer. This aspect of discovering biomarkers using this type of sensor is novel and is based on standard or structured databases.

In one embodiment, the standards or structured database is dependent on the type of sensor and the configuration of the metal oxide sensor array and the constituent metal oxide of the pixel. The database is designed for a particular sensor type and the way the sensor collects the data. There are many types of sensors similar to that of gas sensors for example like electro-chemical sensors. The idea is that the user will use a gas sensor to create the data and thus generate smell information and also receive the smell information related to similar gas sensors from the centralized database.

In other sensor systems, sensing selectivity or specificity can be achieved through material selection (different electrolytes or different nanomaterials) and surface modification or doping. These two approaches can also be used in MOS sensors. In addition, MOS sensors are known to be temperature dependent. Temperature sweeping is the most unique part of the technology and the advantage of doing the temperature sweep is to create another dimension of information that is not existing in other sensor systems, such as electrolyte-based electrochemical sensors, nanomaterial, or carbon nano-tube-based field-effect sensors. Fine step sweeping is the unique method and is performed to create more features from one particular metal oxide. One metal oxide can create numerous data products. Typically, a sweep from 200° C. to 500° C. is performed by choosing the step between the 1° C. to 10° C. For 1° C. sweep steps, a sweeping can generate a couple of hundred data points and, for a 10° C. sweep steps, there can be fewer data points. The idea is to create much data from one particular pixel or metal oxide. Since multiple metal oxide pixels are present in one sensor array, one can create a matrix of data. Other sensors or other methods that use metal oxide will not be able to create such rich data without fine step temperature sweeping. With the rich amount of data, more information from the sensor is created.

In one example, there is provided a method for generating a structured database of multi-dimensional smell information for an analyte in a gas environment for a Metal Oxide Semiconductor (MOS) sensor array having a plurality of MOS sensor pixels, comprising, exposing the plurality of MOS sensor pixels with a MOS active material to the analyte in the gas environment, a heating of the plurality of MOS sensor pixels to a sequence of a different predetermined temperatures via a heating element wherein the heating occurs for a period of time for each of the different predetermined temperatures, detecting a response signal, via an electrode, generated by the plurality of MOS sensor pixels at each of the different predetermined temperatures, assembling of the response signals generated by the plurality of MOS sensor pixels into a digital signature of a smell comprising, a smell data in a two dimensional array and an associated smell condition data, wherein the smell data comprises the different predetermined temperatures along one dimension and the plurality of MOS sensor pixels along another dimension and elements of the two dimensional array are formed by the response signals generated by the plurality of MOS sensor pixels after the response signals of the plurality of MOS sensor pixels are normalized, and wherein the associated smell condition data comprises source of the smell data along with an environmental and a geographical location data.

In one example of a method an array of MOS sensor pixels is employed for detection of the response signals.

In one example of a method each MOS sensor pixel in the array of MOS sensor pixels is heated to different predetermined temperatures simultaneously for the detection of the response signals.

In one example of a method the array of MOS sensor pixels comprises a plurality of individual MOS sensor pixels having different MOS active materials.

In one example of a method the array of MOS sensor pixels comprises at least two individual MOS sensor pixels having different MOS active materials.

In one example of a method the array of MOS sensor pixels comprises two to ten individual MOS sensor pixels having different MOS active materials.

In one example of a method each individual MOS sensor pixel has a different MOS active material.

In one example of a method the array of MOS sensor pixels comprises four individual MOS sensor pixels having different MOS active materials.

In one example of a method the MOS active material is a member selected from the group consisting of: $SnO_2$, $V_2O_5$, $WO_3$, $Cr_{2-x}Ti_xO_3$, $ZnO$, $TeO_2$, $TiO_2$, $CuO$, $CeO_2$, $Al_2O_3$, $ZrO_2$, $V_2O_3$, $Fe_2O_3$, $Mo_2O_3$, $Nd_2O_3$, $La_2O_3$, $Nb_2O_5$, $Ta_2O_5$, $In_2O_3$, $GeO_2$, ITO, or combinations thereof.

In one example of a method in the MOS active material is a member selected from the group consisting of: $In_2O_3$, $SnO_2$, $ZnO$, $WO_3$, or combinations thereof.

In one example of a method the identifying the analyte also identifies a concentration of the analyte based on the comparison of the sample data with the data in the standards database.

In one example of a method the sequence of different temperatures falls within the range of temperatures between 100° C. to 500° C.

In one example of a method the sequence of different predetermined temperatures is split among multiple identical MOS sensor pixels.

In one example of a method the sample data is assembled from the multiple identical MOS sensor pixels.

In one example of a method the sequence of different predetermined temperatures is separated by increments of 5° C. or less.

In one example of a method the sequence of different predetermined temperatures is separated by increments of 20° C. or less.

In one example of a method the period of time is a range of time between 0.2 to 20 seconds, or between 1 to 10 seconds, or two to five seconds.

In one example of a method the analyte is a volatile organic compound (VOC), a vapor, a vaporized solid, or a liquid.

In one example of a method the analyte comprises a plurality of analytes and the identifying identifies each of the plurality of analytes.

In one example of a method the standards database comprises signal data generated by exposing a known analyte to a specific type of MOS sensor pixel, under known conditions.

In one example of a method the database is stored locally to the MOS sensor pixel.

In one example of a method the database is stored remotely to the MOS sensor pixel.

In one example of a method the database is updated with additional information.

In one example of a method, heating the MOS sensor pixel to a predetermined temperature after detecting the response signals to clean any remaining analyte from the MOS sensor pixel.

In one example of a method the sample data forms a spectrum with at least one peak and the at least one peak is employed to identify more than one analyte.

In one example of a method the sample data forms a plurality of peaks, and the plurality of peaks are employed to identify more than one analyte.

In one example of a method the MOS sensor pixel is doped with a dopant to increase sensitivity and selectivity wherein the dopant is selected from the group of dopants consisting of: Pt, Pd, Si, Ti, or a combination thereof.

In one example of a method the power consumption of the MOS sensor pixel is less than one watt.

In one example, there is provided a sensor array operable to detect an analyte, comprising, a support substrate, a plurality of Metal Oxide Semiconductor (MOS) sensor pixels coupled to the substrate, each MOS sensor pixel further comprising a MOS active material configured to be exposed to the analyte, a plurality of heating elements thermally coupled to the MOS active materials of the plurality of MOS sensor pixels in a position and orientation that facilitates heating of the MOS active materials to a plurality of predetermined different temperatures, an electrode functionally coupled to the MOS active material and operable to detect response signals from the MOS active material at each of the plurality of predetermined different temperatures and a temperature controller having circuitry with logic configured to heat the plurality of heating elements to a sequence of predetermined different temperatures for a predetermined period of time for each of the predetermined different temperatures.

In one example of sensor array the plurality of MOS sensor pixels comprises different MOS sensors composed of different oxides.

In one example of sensor array the analyte is a volatile organic compound (VOC), a vapor, a vaporized solid, or a liquid.

In one example of sensor array the analyte comprises a plurality of analytes and the identifying identifies each of the plurality of analytes.

In one example of sensor array the standards database comprises signal data generated by exposing a known analyte to a specific type of MOS sensor pixel, under known conditions.

In one example of sensor array the database is stored locally to the processor.

In one example of sensor array the database is stored remotely to the processor.

In one example of a sensor array the database is updated with additional information.

In one example of sensor array the sample data forms a plurality of peaks and the plurality of peaks are employed to identify more than one analyte.

In one example of sensor array the temperature controller facilitates simultaneous heating of each of the MOS active materials to a different predetermined temperature.

In one example of sensor array the plurality of MOS sensor pixels comprises at least two individual MOS sensor pixels having different MOS active materials.

In one example of sensor array the plurality of MOS sensor pixels comprises two to ten individual MOS sensor pixels having different MOS active materials.

In one example of sensor array each individual MOS sensor pixel has a different MOS active material.

In one example of sensor array the plurality of MOS sensor pixels comprises four individual MOS sensors having different MOS active materials.

In one example of sensor array the e MOS active material is a member selected from the group consisting of: $SnO_2$, $V_2O_5$, $WO_3$, $Cr_{2-x}Ti_xO_3$, ZnO, $TeO_2$, $TiO_2$, CuO, $CeO_2$, $Al_2O_3$, $ZrO_2$, $V_2O_3$, $Fe_2O_3$, $Mo_2O_3$, $Nd_2O_3$, $La_2O_3$, $Nb_2O_5$, $Ta_2O_5$, $In_2O_3$, $GeO_2$, ITO, or combinations thereof.

In one example of sensor array the MOS active material is a member selected from the group consisting of: $In_2O_3$, $SnO_2$, ZnO, $WO_3$, or combinations thereof.

In one example of sensor array the MOS sensor pixel is doped with a dopant to increase sensitivity and selectivity wherein the dopant is selected from the group of dopants consisting of: Pt, Pd, Si, Ti, or a combination thereof.

In one example of sensor array a power consumption of the MOS sensor pixel is less than one watt.

In one example of sensor array the support substrate comprises a suspended membrane to reduce heat dissipation and power consumption.

one example, there is provided a device operable to identify an analyte, comprising, a housing comprising, a sensor array as recited herein, a support substrate coupled to the plurality of Metal Oxide Semiconductor (MOS) sensor pixels of the sensor array, the temperature controller with logic configured to, control the plurality of heating elements to heat the plurality of MOS sensor pixels to a variety of predetermined temperatures wherein the plurality of MOS sensor pixels are heated to each of the predetermined temperatures for a period of time or to simultaneously heat each of the plurality of MOS sensor pixels to a different predetermined temperature, a processor with logic configured to, assemble the response signals into sample data with data features for machine learning, compare the sample data with data in a standards database;

identify a composition of the analyte based on the comparison of the data features and a communication component configured to communicate the identity of the analyte to a display.

In one example, there is provided a system operable to identify an analyte, comprising, a sensor array as recited herein, a support substrate coupled to the plurality of Metal Oxide Semiconductor (MOS) sensor pixels of the sensor array, the temperature controller with logic configured to, control the plurality of heating elements to heat the plurality of MOS sensors to a variety of predetermined temperatures wherein the plurality of MOS sensor pixels are heated to each of the predetermined temperatures for a period of time or to simultaneously heat each of the plurality of MOS sensor pixels to a different predetermined temperature, a processor with logic configured to, assemble the response signals into sample data with data features for machine learning, compare the sample data with data in a standards database, identify a composition of the analyte based on the data features and a communication component configured to communicate the identity of the analyte to a display.

A system for generating a structured database of multi-dimensional smell information for an analyte in a gas environment comprising, a Metal Oxide Semiconductor (MOS) sensor array having a plurality of MOS sensor pixels with a MOS active material, a temperature controller with a logic configured to, control a plurality of heating elements to heat the plurality of MOS sensor pixels to a variety of predetermined temperatures wherein the plurality of MOS sensor pixels are heated to each of the predetermined temperatures for a period of time or to simultaneously heat each of the plurality of MOS sensor pixels to a different predetermined temperature, a processor with logic configured to, assemble the response signals generated by the plurality of MOS sensor pixels into a digital signature of a smell comprising, a smell data in a two dimensional array and an associated smell condition data, wherein the smell data comprises the different predetermined temperatures along one dimension and the plurality of MOS sensor pixels along another dimension and elements of the two dimensional array are formed by the response signals generated by the plurality of MOS sensor pixels after the response signals of the plurality of MOS sensor pixels is normalized, and wherein the associated smell condition data comprises source of the smell data along with an environmental and a geographical location data and a communication component configured to communicate the smell information to a local memory and/or to a cloud and/or to a display.

In an embodiment, it is a database stored in a computer readable storage medium, the database comprising, a digital signature of a smell comprising a smell data stored in a data structure on the computer readable storage medium, wherein the computer readable storage medium comprises a memory having a computer executable program code stored thereon, the smell data comprises response signals arranged in a two-dimensional tabular form, wherein the two-dimensional tabular form comprises a plurality of a first vectors corresponding to a material type, a plurality of a second vectors corresponding to a sequence of predetermined stimulus, and a plurality of cells at intersections of the plurality of a first vectors and the plurality of a second vectors, an associated smell condition data appended to the smell data, wherein the associated smell condition data comprises conditions under which the smell data was generated, and an index for the smell data; wherein the computer executable program code is executable to analyze a smell received in a query.

In an embodiment, it is a database structure for a digital signature of a smell comprising, a core smell data from a Metal Oxide Semiconductor (MOS) sensor array having a plurality of pixels comprising an MOS active material type wherein the core smell data comprises response signals generated by each of the MOS active material type at a sequence of predetermined temperatures arranged in a two-dimensional tabular form wherein a plurality of a first vector correspond to Metal Oxide Semiconductor (MOS) active material type, a plurality of a second vector corresponding to a sequence of predetermined temperatures, and a plurality of cells formed by intersecting the plurality of a first vector and the plurality of a second vector holding a response signal of the MOS active material type corresponding to a first vector at the sequence of predetermined temperature corresponding to the a second vector; and an associated smell condition data appended to the core smell data wherein the associated smell condition data comprises source of the core smell data, an environmental humidity, a geographical location data, a temperature data at the geographical location and a date and time of the core smell data generation, wherein the database comprises a structured smell data of the smell generated by an analyte in a gas environment by the Metal Oxide Semiconductor (MOS) sensor array.

In an embodiment, it is a method for generating a multi-dimensional smell information comprising, exposing a plurality of MOS sensor pixels having an MOS active material of a Metal Oxide Semiconductor (MOS) sensor array to the analyte in the gas environment, heating the plurality of MOS sensor pixels to a sequence of a different predetermined temperatures via heating elements wherein the heating occurs for a period of time for each of the different predetermined temperatures, detecting response signals, via pixel electrodes, generated by the plurality of MOS sensor pixels at each of the different predetermined temperatures, assembling of the response signals generated by the plurality of MOS sensor pixels into a database for a digital signature of a smell comprising, a core smell data formed from response signals generated by each of the MOS active material type at a sequence of predetermined temperatures arranged in a two-dimensional tabular form wherein a plurality of a first vector correspond to Metal Oxide Semiconductor (MOS) active material type, a plurality of a second vector corresponding to a sequence of predetermined temperatures, and a plurality of cells formed by intersecting the plurality of a first vector and the plurality of a second vector holding a response signal of the MOS active material type corresponding to the row at the sequence of predetermined temperature corresponding to the column and an associated smell condition data appended to the core smell data wherein the associated smell condition data comprises source of the core smell data, an environmental humidity, a geographical location data, a temperature data at the geographical location and a date and time of the core smell data generation, wherein the database comprises a structured smell information of the smell generated by an analyte in a gas environment by the Metal Oxide Semiconductor (MOS) sensor array.

In an embodiment, it is a system, comprising, a Metal Oxide Semiconductor (MOS) sensor array having a plurality of MOS sensor pixels with a MOS active material, a temperature controller with a logic configured to, control a plurality of heating elements to heat the plurality of MOS sensor pixels to a variety of predetermined temperatures wherein the plurality of MOS sensor pixels are heated to each of the predetermined temperatures for a period of time or to simultaneously heat each of the plurality of MOS sensor pixels to a different predetermined temperature, a processor with logic configured to, assemble the response signals generated by the plurality of MOS sensor pixels into a database for a digital signature of a smell comprising, a core smell data formed from response signals generated by each of the MOS active material type at a sequence of predetermined temperatures arranged in a two-dimensional tabular form wherein a plurality of a first vector correspond to Metal Oxide Semiconductor (MOS) active material type, a plurality of a second vector corresponding to a sequence of predetermined temperatures, and a plurality of cells formed by intersecting the plurality of a first vector and the plurality of a second vector holding a response signal of the MOS active material type corresponding to the row at the sequence of predetermined temperature corresponding to the column and an associated smell condition data appended to the core smell data wherein the associated smell condition data comprises source of the core smell data, an environmental humidity, a geographical location data, a temperature data at the geographical location and a date and time of the core smell data generation, wherein the database comprises a structured smell information of the smell generated by an analyte in a gas environment by the Metal Oxide Semiconductor (MOS) sensor array.

In an embodiment, it is a smell analysis system, comprising, a Metal Oxide Semiconductor (MOS) sensor array having a plurality of MOS sensor pixels with a MOS active material, a smell database comprising a digital signature of a smell, a core smell data formed from response signals generated by each of the MOS active material type at a sequence of predetermined temperatures arranged in a two-dimensional tabular form wherein a plurality of a first vector correspond to Metal Oxide Semiconductor (MOS) active material type, a plurality of a second vector corresponding to a sequence of predetermined temperatures, and a plurality of cells formed by intersecting the plurality of a first vector and the plurality of a second vector holding a response signal of the MOS active material type corresponding to the row at the sequence of predetermined temperature corresponding to the column and an associated smell condition information appended to the core smell information wherein the associated smell condition information comprises source of the core smell data, an environmental humidity, a geographical location data, a temperature data at the geographical location and a date and time of the core smell data generation, wherein the database comprises a structured smell information of the smell generated by an analyte in a gas environment by the Metal Oxide Semiconductor (MOS) sensor array, a query interface for receiving a query relating to a smell to the smell database, at least one processor and a memory in communication with the at least one processor, wherein the at least one processor is programmed to perform operations for smell comparison coupled with the smell database and having a plurality of regression models and one or more artificial neural networks, to analyze a response pattern of the MOS sensor to a smell from the smell database using one or more of the plurality of regression models and the one or more artificial neural networks.

In one embodiment, the digital signature of a smell comprises binary data and is used to digitize smell by the computer and computer-based devices.

In one example, the database comprises a plurality of digital signatures of smell comprising smell data for a plurality of smells and can be updated for smells from additional analytes.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system, comprising:
    a sensor,
    a heating element thermally coupled to the sensor,
    a control module, wherein the control module is configured for monitoring a temperature of the sensor and controlling the heating element to generate a stimulus;
    a database;
    a processor; and
    a memory in communication with the processor, wherein the processor, under power, performs an operation for comparing a sample smell with a smell in the database to analyze a response pattern of the smell from the sensor in the database with the sample smell using a computer executable program code;
    the database comprising:
        a digital signature of the smell comprising a smell data, wherein the smell data comprises a response signal that is a function of a first data corresponding to a material type generating the response signal and a second data corresponding to the stimulus operable to generating the response signal, wherein the smell data is stored in a data structure on a computer readable storage medium that is associated with the computer executable program code and wherein the response signal is a measurable response of the generator to the stimulus that is a function of change in electrical properties of at least one of a resistance and impedance in the generator;
        a smell condition data associated with the smell data, wherein the smell condition data comprises a condition under which the smell data was generated;
        an index for the smell data;
        a query interface for receiving a query for the sample smell; and
        wherein the data structure comprises the smell data arranged in at least one of a computer-readable matrix and a heat-map format; and
        wherein the system is configured to analyze the sample smell.

2. The system of claim 1, wherein the sensor is a Metal Oxide Semiconductor (MOS) sensor array having a plurality of MOS sensor pixels with a MOS active material.

3. The system of claim 1, wherein the smell condition data associated with the smell data comprises source of smell data, an environmental humidity, a geographical location data, a temperature data at a geographical location and a date and time of generating the smell data.

4. The system of claim 1, wherein the first data corresponding to the material type is an MOS active material type.

5. The system of claim 1, wherein the second data corresponding to the stimulus is a sequence of temperatures.

6. The system of claim 1, further comprises an environmental analysis module enabled to perform at least one of a temperature scanning, a comparison of spectrum like data with at least one peak, a pattern recognition, a pattern extrapolation, a quantitative analysis, a qualitative analysis, an environmental analysis, and a system status analysis.

7. The system of claim 1, wherein the database is stored locally or stored remotely to a cloud network.

8. A non-transitory machine readable storage medium having instructions embodied thereon for encoding a method configured for creating and using a database, the database comprising:
    a digital signature of a smell comprising a smell data, wherein the smell data comprises a response signal that is a function of a first data corresponding to a material type generating the response signal and a second data corresponding to a stimulus for generating the response signal;
    a smell condition data associated with the smell data, wherein the smell condition data comprises a condition under which the smell data was generated; and
    an index for the smell data;
    wherein the smell data is stored in a data structure on a computer readable storage medium that is associated with a computer executable program code; and
    wherein the data structure comprises the smell data arranged in at least one of a computer-readable matrix and a heat-map format;
    wherein the response signal is a measurable response of the generator to the stimulus that is a function of change in electrical properties of resistance or impedance in the generator;
    wherein a sample smell is analyzed by comparing with the smell data in the database using the computer executable program code; and
    wherein the method is configured for identifying an unknown smell.

9. The non-transitory machine readable storage medium of claim 8, wherein the smell data is normalized and a heatmap is generated.

10. The non-transitory machine readable storage medium of claim 8, wherein the first data corresponding to the material type is MOS active material type selected from the group consisting of: $SnO_2$, $V_2O_5$, $WO_3$, $ZnO$, $TeO_2$, $TiO_2$, $CuO$, $CeO_2$, $Al_2O_3$, $ZrO_2$, $V_2O_3$, $Fe_2O_3$, $Mo_2O_3$, $Nd_2O_3$, $La_2O_3$, $Nb_2O_5$, $Ta_2O_5$, $In_2O_3$, $GeO_2$, ITO, or combinations thereof.

11. The non-transitory machine readable storage medium of claim 8, wherein the smell condition data comprises source of the smell data, an environmental humidity, data of a geographical location, a temperature data at the geographical location and a date and a time of generation of the smell data.

12. The non-transitory machine readable storage medium of claim 8, wherein the computer executable program code uses mathematical techniques to analyze the smell and uses normalized values of the smell data.

13. The non-transitory machine readable storage medium of claim 8, wherein the computer executable program code uses image processing tools or image recognition tools for querying the smell and uses heatmap of the smell.

14. The non-transitory machine readable storage medium of claim 8, wherein the method is configured for monitoring changes in the smell over time in a given location.

15. The non-transitory machine readable storage medium of claim 8, wherein the method is configured for tracking of the sample smell over a time and a location.

16. The non-transitory machine readable storage medium of claim 8, wherein the method is configured for discovering unique features associated with given smell conditions.

17. The non-transitory machine readable storage medium of claim 8, wherein the method is configured for mapping location distribution of the smell using the database.

18. A non-transitory machine readable storage medium having instructions embodied thereon for encoding a database comprising a database structure comprising:
- a digital signature of a smell comprising a smell data, wherein the smell data comprises a response signal that is a function of a first data corresponding to a material type generating the response signal and a second data corresponding to a stimulus operable to generating the response signal;
- a smell condition data associated with the smell data, wherein the smell condition data comprises a condition under which the response signal was generated; and
- an index for the smell data;
- wherein the smell data is stored in a data structure on a computer readable storage medium that is associated with a computer executable program code that is configured to analyze a sample smell;
- wherein the data structure comprises the smell data arranged in at least one of a computer-readable matrix and heat-map format;
- wherein the response signal is a measurable response of the generator to the stimulus that is a function of change in electrical properties of resistance or impedance in the generator; and
- wherein the computer executable program code is configured for identifying an unknown smell.

* * * * *